United States Patent [19]

Wallner et al.

[11] Patent Number: 4,874,743

[45] Date of Patent: Oct. 17, 1989

[54] DNA SEQUENCES, RECOMBINANT DNA MOLECULES AND PROCESSES FOR PRODUCING HUMAN PHOSPHOLIPASE INHIBITOR-LIKE POLYPEPTIDES

[75] Inventors: Barbara P. Wallner, Cambridge; R. Blake Pepinsky, Watertown; Jeffrey L. Garwin, Bedford, all of Mass.

[73] Assignee: Biogen, Inc., Cambridge, Mass.

[21] Appl. No.: 712,376

[22] Filed: Mar. 15, 1985

Related U.S. Application Data

[63] Continuation-in-part of Ser. No. 690,146, Jan. 10, 1985.

[51] Int. Cl.$^4$ ...................... A61K 37/02; C07K 13/00
[52] U.S. Cl. ...................................... 514/12; 530/350
[58] Field of Search ................... 435/68, 172.3, 240.2, 435/240.4, 253, 254, 255, 320; 530/350; 514/2, 12

[56] References Cited

U.S. PATENT DOCUMENTS

| | | | |
|---|---|---|---|
| 4,239,780 | 10/1980 | Wallach | 424/330 |
| 4,394,443 | 7/1983 | Weissman et al. | 435/6 |
| 4,530,901 | 7/1985 | Weissmann | 435/70 |
| 4,537,858 | 8/1985 | O'Sullivan et al. | 435/119 |

FOREIGN PATENT DOCUMENTS

WO86/06100 10/1986 PCT Int'l Appl. .

OTHER PUBLICATIONS

Chem. Abstr., vol. 99, (1983), 86478.
Chem. Abstr., vol. 100, (1984), 119189.
P. Dimond, "Biogen Produces Recombinant Anti-Inflammatory Agent", *Genetic Engineering News*, 5, p. 12, (1985).
E. Erickson et al., "Identication of a Cellular Protein Substrate Phosphorylated by the Avian Sarcoma Virus Transforming Gene Product", *Cell*, 21, pp. 829–836, (1980).
E. Erickson et al., "Biochemical Characterization of a 34 Kilodalton Normal Cellular Substrate of pp60$^{v-src}$ and an Associated 6-Kilodalton Protein", *Mol. Gen. Biol.*, 4, pp. 77–85, (1984).
J. Etienne and J. Polonovski, "Phospholipase A$_2$ Activity in Rat and Human Lymphocytes", *Biochem. and Biophys. Res. Comm.*, 125, pp. 719–727, (1984).
K. Radke et al., "Transformation by Rous Sarcoma Virus: A Cellular Substrate for Transformation-Specific Protein Phosphorylation Contains Phosphotyrosine", *Cell*, 21, pp. 821–888, (1980).
"Biogen Produces Anti-Inflammatory Agent; Davies Resigns", *Genetic Engineering Letter*, p. 4, Jun. 10, 1985.
G. J. Blackwell et al., "Glucocorticoids Induce the Formation and Release of Anti-Inflammatory and Anti-Phospholipase Proteins into the Peritoneal Cavity of the Rat", *Br. J. Pharmac.*, 76, pp. 185–194, (1982).
E. F. Davidson et al., "Inhibition of Phospholipase A$_2$ by Lipocortins and Calpactins", *J. Biol. Chem.*, 262, pp. 1698–1705, (1987).
M. DiRosa et al., "Anti-Phospholipase Proteins", *Prostaglandins*, 28, pp. 441–442, (1984).
M. Errasfa et al., "The Presence of Lipocortin in Human Embryonic Skin Fibroblasts and Its Regulation by Anti-Inflammatory Steriods", *Biochemica et Biophysica Acta*, 847, pp. 247–254, (1985).
R. Fava and S. Cohen, "Isolation of a Calcium-Dependent 35 Kilodalton Substrate for the Epidermal Growth Factor Receptor/Kinase from A-431 Cells", *J. Biol. Chem.*, 259, pp. 2636–3645, (1984).

(List continued on next page.)

*Primary Examiner*—Delbert R. Phillips
*Attorney, Agent, or Firm*—James F. Haley, Jr.; Denise L. Loring; David J. Meyer

[57] ABSTRACT

DNA sequences, recombinant DNA molecules and hosts transformed with them which produce human phospholipase inhibitor-like polypeptides and methods of making and using these products. The DNA sequences and recombinant DNA molecules are characterized in that they code on expression for a human phospholipase inhibitor-like polypeptide. In appropriate hosts these DNA sequences permit the production of human phospholipase inhibitor-like polypeptides useful as anti-inflammatory agents and methods in the treatment of arthritic, allergic, dermatologic, ophthalmic and collagen diseases as well as other disorders involving inflammatory processes.

9 Claims, 10 Drawing Sheets

OTHER PUBLICATIONS

R. J. Flower and G. J. Blackwell, "Anti-Inflammatory Steriods Induce Biosynthesis of a Phospholipase $A_2$ Inhibitor which Prevents Prostaglandin Generation", *Nature*, 278, pp. 456-459, (1979).

R. J. Flower et al., "Macrocortin and the Mechanism of Action of the Glucocorticoids", *Advances in Inflammation Research*, 7, pp. 61-70, (1984).

M. J. Geisow, "Common Domain Structure of $Ca+^2$ and Lipid Binding Proteins", *FEBS Letters*, 203, pp. 99-103, (1986).

M. J. Geisow and J. H. Walker, "New Proteins Involved in Cell Regulation by $Ca^{2+}$ and Phospholipids", *Trends Biochem. Sci.*, 11, pp. 420-423, (1986).

V. Gerke and K. Weber, "Identity of p36K Phosphorylated Upon Rous Sarcoma Virus Transformation with a Protein Purified from Brush Borders; Calcium-Dependent Binding to Non-Erythroid Spectrin and F-Actin", *EMBO Journal*, 3, pp. 227-233, (1984).

V. Gerke and K. Weber, "Calcium-Dependent Conformational Changes in the 36-kDa Subunit of Intestinal Protein I Related to the Cellular 36-kDa Target of Rous Sarcoma Virus Tyrosine Kinase", *J. Biol. Chem.*, 260, pp. 1688-1695, (1986).

J. Glenney et al., "Amino-Teminal Sequence of p36 and Associated p10: Identification of The Site of Tyrosine Phosphorylation and Homolgy with S-100", Proc. Nat. Acad. Sci. U.S.A., 82, pp. 7884-7888, (1985).

T. Hattori et al., "Inhibition of Human Natural Killer (NK) Activity and Antibody Dependent Cellular Cytotoxicity (ADCC) by Lipomodulin, A Phospholipase Inhibitory Protein", *J. Immunol.*, 131, pp. 662-665, (1983).

F. Hirata et al., "A Phospholipase $A_2$ Inhibitory Protein in Rabbit Neutrophils Induced by Glucocorticoids", *Proc. Nat. Acad. Sci. U.S.A.*, 77, pp. 2533-2536, (1980).

F. Hirata et al., "Presence of Autoantibody for Phospholipase Inhibitory Protein, Lipomodulin in Patients with Rheumatic Disease", *Proc. Nat. Acad. Sci. U.S.A.*, 78, pp. 3190-3994, (1981).

F. Hirata, "Roles of Liomodulin: A Phospholipase Inhibitory Protein in Immunoregulation", *Adv. Inf. Res.* 7, pp. 71-78, (1984).

F. Hirata et al., "Inhibition of Leukocyte Chemotaxis by Glu-Glu-Glu-Glu-Tyr-Pro-Met-Glu and Leu-Ile-Glu-Asp-Asn-Glu-Tyr-Thr-Ala-Arg-Gln-Gly", *Biochem. and Biophys. Res. Comm.*, 118, pp. 682-690, (1984).

F. Hirata et al., "Isolation and Characterization of Lipocortin (Lipomodulin)", *Agents and Actions*, 17, pp. 263-266, (1985).

K. Huang et al., "Two Human 35 kd Inhibitors of Phospholipase $A_2$ are Related to Substrates of $pp60^{v-src}$ and of the Epidermal Growth Factor Receptor/Kianse", *Cell*, 46, pp. 191-199, (1986).

R. H. Kretsinger et al., "Consensus in Exocytosis", *Nature*, 320, p. 573, (1986).

I. Mancheva et al., "The Primary Structure of the Inhibitor of Vipoxin from the Venom of the Bulgarian Viper (*Vipera ammodytes* ammodytes, Serpentes)", *Hoppe-Selye's Z. Physiol. Chem.*, 365, pp. 885-894, (1984).

I. Mancheva et al., "Sequence Homology Between Phospholipase and Its Inhibitor in Shake Venom: The Primary Structure of the Inhibitor of Vipoxin from the Venom of the Bulgarian Viper", *Biol. Abstr.*, 79, #39874, (1984).

T. Maniatis et al., *Molecular Cloning a Laboratory Manual*, pp. 5-6, 405-414, (1984).

J. F. Morrow, "Recombinant DNA Techniques", *Methods in Enzymology*, 68, pp. 3-24, (1979).

Oroszlan et al., "Amino- and Carboxyl-Terminal Amino Acid Sequences of Proteins Coded by the gag Gene of Murine Leukemia Virus", *Proc. Nat. Acad. Sci. U.S.A.*, 75, pp. 1404-1408, (1977).

R. B. Pepinsky et al., "Localization of Lipid-Protein and Protein-Protein Interactions Within the Murine gag Precursor by a Novel Peptide-Mapping Technique", *J. Biol. Chem.*, 258, pp. 11229-11235, (1983).

R. B. Pepinsky and L. K. Sinclair, "Epidermal Growth Factor-Dependent Phosphoylation of Lipocortin", *Nature*, 321, pp. 81-84, (1986).

R. B. Pepinsky et al., "Purification and Partial Sequence Analysis of a 37-kDa Protein that Inhibits Phospholipase $A_2$ Activity from Rat Peritoneal Exudates", *J. Biol. Chem.*, 261, pp. 4239-4246, (1986).

C. J. M. Saris et al., "The cDNA Sequence for the Protein-Tyrosine Kinase Substrate p36, (Calpactin I Heavy Chain) Reveals a Multidomain Protein With Internal Repeats", *Cell*, 46, pp. 201-212, (1986).

T. Ueda et al., "Suppression of IgE Synthesis in Mouse Plasma Cells and B Cells by Rat IgE-Suppressive Factor", *J. Immunol.*, 133, pp. 803-808, (1984).

B. P. Wallner et al., "Cloning and Expression of Human Lipocortin, A. Phospholipase $A_2$ Inhibitor with Potential Anti-Inflammatory Activity", *Nature*, 320, pp. 77-81, (1986).

FIG. 1

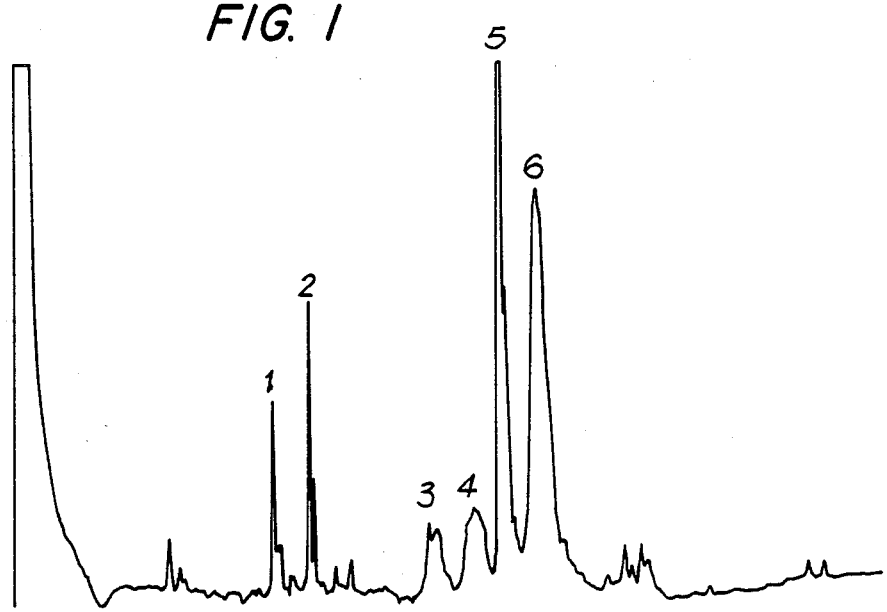

CNBr 1: (less than 2 Kd based on amino acid analysis)

- met - lys - gly - ala - gly - thr - arg - arg - lys - thr -
   1     2     3     4     5     6     7     8     9    10 leu - ile -
     11    12

CNBr 2: (less than 2 Kd based on amino acid analysis)

- met - leu - lys - thr - pro - ala - gln - phe - asp - ala -
   1     2     3     4     5     6     7     8     9    10 asp - glu - leu - ile(?) - arg(?)
     11    12    13     14      15

CNBr 3: (7 Kd based on SDS-polyacrylamide gel electrophoresis)

- met - $\frac{tyr}{lys}$ - $\frac{val}{ala}$ - asn - gln - asp - $\frac{leu}{trp}$ - ala - $\frac{ala}{gln}$ -
   1     2      3      4     5     6     7     8     9

CNBr 4: (no protein detected by SDS-PAGE)

CNBr 5: (mixture of peptides, less than 5 Kd based on SDS-PAGE)

CNBr 6: (mixture consisting of two 12 Kd fragments based on SDS-PAGE)

FIG. 2

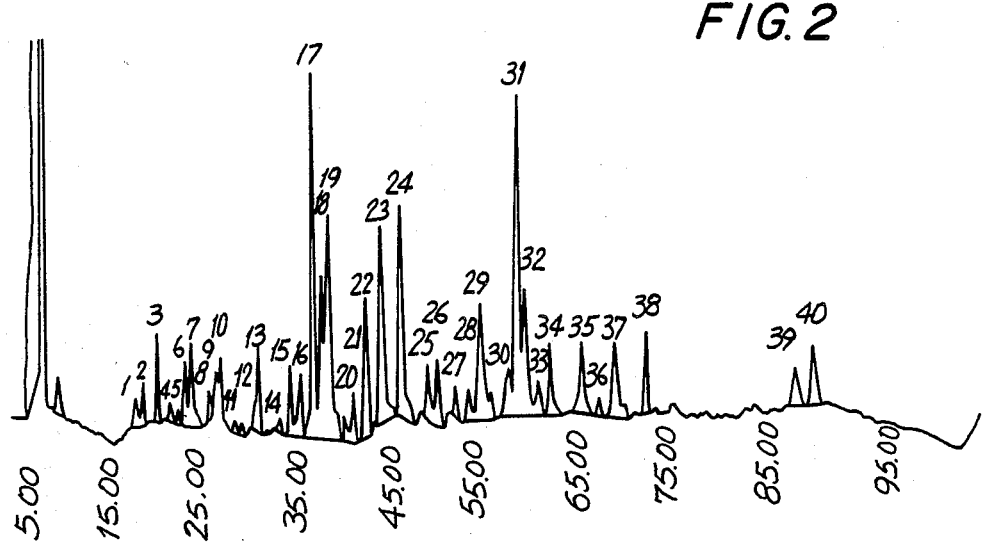

```
T17(a+b):   - ala - leu - gln - gln - ala - tyr - gln - arg
              tyr   phe   val   gln   lys   gly         gly
               1     2     3     4     5     6     7     8

T22(a):     - ser - glu - ile - asp - met - asn - glu - ile - lys
               1     2     3     4     5     6     7     8     9

T22(b):     - lys - val - phe - gln - asn - tyr - arg
               1     2     3     4     5     6     7

T23:        - ser - tyr - pro - his(arg) - leu
               1     2     3       4        5

T24:        - thr - pro - ala - gln - phe - asp - ala - asp - glu -
               1     2     3     4     5     6     7     8     9
              leu - leu - arg
               10    11    12

T29:        - ala - ala - tyr - leu - gln - glu - thr - gly - lys -
               1     2     3     4     5     6     7     8     9
              pro - leu - asp - glu - thr - leu - lys
               10    11    12    13    14    15    16

T31:        - gly - gly - pro - gly - ser - ala - val - ser - pro -
               1     2     3     4     5     6     7     8     9
              tyr - pro - ser(thr) - phe - asn - ser(thr) - ser -
               10    11      12       13    14      15       16
              ser - thr - val - ala - trp - ala -
               17    18    19    20    21    22

T35:        - lys - gly - thr - asp - val - asn - val - phe(?) -
               1     2     3     4     5     6     7      8
              asn - thr - x   - leu
               9     10    11    12

T38:        - gly - leu - gly - thr - asp - glu -
               1     2     3     4     5     6
```

FIG. 3

Sequence T22a:  GluILeAspMetAsnGluIle
20-mer          GARATHGAYATGAAYGARAT

Sequence T22b:  LysValPheGlnAsnTyr
17-mer          AARGTNTTYCARAAYTA

Sequence T24[1]: AlaGlnPheAspAlaAspGlu
20-mer          GCNCARTTYGAYGCNGAYGA

Sequence T29:   GlnGluThrGlyLysPro
17-mer          CARGARACNGGNAARCC

[1] The sequence shown for T24 is also contained within CNBr fragment 2.

Coding redundancies are:

```
1     TTTCTCTTTAGTTCTTTGCAAGAAGGTAGAGATAAAGACACTTTTCAAAAATGGCAATGGTATCAGAATTCCTCAAGCAGGCCTGGTTTATTGAAAATG
      ----------------------------------------------------------------------------------------------------

101   AAGAGAAATCAAGAAACGTTCTTCCATCTCTATTTCTGAAAAAGTTTTTACCGTTACCATAGTCTTAAGGAGTTCGTCCGGACCAATAACTTTTAC
      ----------------------------------------------------------------------------------------------------
      PheLeuPheSerLeuGlnGluArgSerSerLysGlyArgAspLysAspThrPheSerLysMetAlaMetValSerGluPheLeuLysGlnAlaTrpPheIleGluAsnG

201   AAGACAGGAATATGTTCAAACTGTGAAGTCATCCAAAGGTGGTCCCGGATCAGCGGTGAGCCCTATCCTACCTTCAATCCATCCTCGGATGTCCGCTGC
      ----------------------------------------------------------------------------------------------------

TTCTCGTTCCTTATACAAGTTTGACACTTCAGTAGGTTTCCACCAGGCCTGCCTCGGGATAGGATGGAAGTTAGGAGCCTAGGACGCTACAGCGACG
      ----------------------------------------------------------------------------------------------------
      luGluGlnGluTyrValGlnThrValLysSerSerLysGlyGlyProGlySerAlaValSerProTyrProTyrPheAsnProSerSerAspValAlaAl

CTTGCATAAGGCCATAATGGTTAAAGGTGTGGATGAAGCAACCATCATTGACATTCTAACTAAGCGAAACATGCACAGCGTCAACAGATCAAGCAGCA
      ----------------------------------------------------------------------------------------------------

301   GAACGTATTCCGGTATTACCAATTTCCACACCTACTTCGTTGGTAGTAACTGTAAGATTGATTCGCTTTGTTACGTCGCAGTTGTCTAGTTTCGTCGT
      ----------------------------------------------------------------------------------------------------
      aLeuHisLysAlaIleMetValLysGlyValAspGluAlaTheIleIleAspIleLeuThrLysArgAsnAsnAlaGlnArgGlnIleLysAlaAla

TATCTCCAGGAAACAGGAAAGCCCCTGGATGAAACACTTAAGAAAGCCCTTACAGGTCACCTTGAGGAGGTTGTTTAGCTCTGCTAAAACTCCAGCGC
      ----------------------------------------------------------------------------------------------------

401   ATAGAGGTCCCTTTGTCCTTCGGGACCTACTTTGTGAATTCTTTCGGGAATGTCCAGTGGAACTCCTCCAACAAAATCGAGACGATTTTGAGGTCGCG
      ----------------------------------------------------------------------------------------------------
      TyrLeuGlnGluThrGlyLysProLeuAspLysLysLysAlaLeuThrGlyHisGlyHisLeuGluValLeuGluValValLeuLeuLysThrProAlaG

AATTTGATGCTGATGAACTTCGTGCTGCCATGAAGGGCCTTGGAACTGATGAAGATACTCTAATTGAGATTTGGCATCAAGAACTAACAAAGAAATCAG
      ----------------------------------------------------------------------------------------------------

501   TTAAACTACGACTACTTGAAGCACGACGACGGTACTTCCCGGAACCTGACTCTTCTATGAGATTAACTCTAAACCGTAGTTCTTGATTGTTCTTTAGTC
      ----------------------------------------------------------------------------------------------------
      lnPheAspAlaAspArgLeuArgAlaAlaMetLysGlyLeuArgThrAspGluAspThrLeuIleGluIleLeuAlaSerArgThrAsnLysGluIleAr

AGACATTAACAGGGTCTACAGAGGAACTGAAGAGAACTGGCCAAAGACATAACCTCAGACAACCTCAGACACATCTGGAGATTTTCGGAACGCTTTCTTT
      ----------------------------------------------------------------------------------------------------

601   TCTGTAATTGTCCCAGATGTCTCCCTTGACTTCTCCTGACTTCTCTGTATTGGAGTCTGTCTAGACCTCTAAAAGCCTTGCGAAACGAAAGAGAA
      ----------------------------------------------------------------------------------------------------
      gAspIleAsnArgValTyrArgValTyrArgGluLeuLysArgAspLeuAlaLysAspIleThrSerAspThrSerGlyPheArgAsnAlaLeuLeuSerLeu

GCTAGGGTGACCGATCTGAGGACTTTGGTGTGAATGAAGACTTGGCTGATTCAGATGCCAGGCCTTGTATGAAGCAGGAGAAAGGAGAAAGGGGACAG
      ----------------------------------------------------------------------------------------------------

CGATTCCCACTGGCTAGACTCCTGAAACCACACTTACTTCTGAACCGACTAAGTCTACGGTCCCGGAACATACTTCGTCCTCCTTTCCCCTGTC
      ----------------------------------------------------------------------------------------------------
      AlaLysGlyAspArgSerGluArgGluAspPheGlyValAsnGluAspLeuAlaAspSerAspAlaArgAlaLeuTyrGluAlaGlyGluArgLysGlyTyrThrA
```

FIG. 4 (cont'd)

```
701  ACGTAAACGTGTTCAATACCATCCTTACCACCAGAAGCTATCCACAACTTCCAGAGTGTTCAGAAATACACCAAGTACAGTAAGCATGACTGAACAA    800
     ----------------------------------------------------------------------------------------------
     TGCATTTGCACAAGTTATGCTAGGAATGGTGGTCTTCGATAGGTCTTGAAGCGTCTCACAAGTCTTATGTGTTCATGTCTATTCGTACTGTACTTGTT
     spValAsnValPheAsnThrIleLeuThrArgSerTyrProGlnLeuArgValPheGlnLysTyrThrLysTyrSerLysIleAspMetAsnLy

801  AGTTCTGGACCTGGAGTTGAAAGTGACATTGAGAAATGCCTCACAGCTATCGTGAAGTGCGCCACAAGCAAACCAGCTTCTTTGCAGAGAAGCTTCAT    900
     ----------------------------------------------------------------------------------------------
     TCAAGACCTGGACCTCAACTTCCACTGTAACTCTTTACGGAGTGTCGATAGCACTTCACGCGGTGTTCGTTGGTCGAAAGAAACGTCTCTTCGAAGTA
     sValLeuAspLeuLeuLysGlyAspIleGluLysCysLeuThrAlaIleValLysCysAlaThrSerLysProAlaPhePheAlaGluLysLeuHis

901  CAAGCCATGAAAGGTGTTGGAACTCGCCATAAGGCATTGATCAGGATTATGGTTCCCGTTCTGAAATTGACATGAATGATATCAAAGCATTCTATCAGA    1000
     ----------------------------------------------------------------------------------------------
     GTTCGGTACTTTCCACAACCTTGAGGCGTATTCCGTAACTAGTCCTAATACCAAGGGCAAGACTTAACTGTACTACTAGTTCGTAAGATAGTCT
     GlnAlaMetLysGlyValGlyThrArgHisLysGlnAlaIleLeuIleArgIleMetValSerArgSerGluIleAspMetAsnAspIleLysAlaPheTyrGlnL

1001 AGATGTATGGTATCTCCCTTTGCCAAGCCATCCTGGATGAAACCAAAGGAGATTATGAGAAAATCTGGTGGCTCTTTGTGGAGGAAACTAAACATTCCC    1100
     ----------------------------------------------------------------------------------------------
     TCTACATACCATAGAGGGAAACGTTCGGTAGGACCTACTTGGTTCCTCTAATACTCTTTAGGACCACCGAGAAACACCTCCTTTGATTGTAAGGG
     ysMetTyrGlyIleSerLeuCysGlnAlaIleLeuAspGluThrLysGlyAspTyrGluLysIleValAlaLeuCysGlyAsnEnd

1101 TTGATGGTCTCAAGCTATGATCAGAAGACTTTAATTATATATTTTCATCCTATAAGCTTAAATAGGAAAGTTCTTCAACAGGATTACAGTGTAGCTACC    1200
     ----------------------------------------------------------------------------------------------
     AACTACCAGAGTTCGATACTAGTCTTCTGAAATTAATATATAAAGTAGGATATCGAATTTATCCTTCAAAGAAGTTGTCTCCTAATGTCACATCGATGG

1201 TACATGCTGAAAAATATAGCCTTTAAATCATTTTTATATTTATATTATAACTCTGTATAATAGATAAGTCCATTTTTTAAAAATGTTTTCCCAAACCATAAAA    1300
     ----------------------------------------------------------------------------------------------
     ATGTACGACTTTTTATATCGGAAATTTAGTAAAATATAATATATTGAGACATATTATCTCTATTCAGGTAAAAATTTTTACAAAAGGGGTTTGGTATTTT

1301 CCCTATACAAGTTGTTCTAGTAACAATACATGAAAGATGTCTATGCTGAAAATAAAATGACGTCACAAGAC                               1376
     ----------------------------------------------------------------------------------------------
     GGGATATGTTCAACAAGATCATTGTTATGTACTCTTCTACAGATACATCGACTTTTATTTACTGCAGTGTTCTG
```

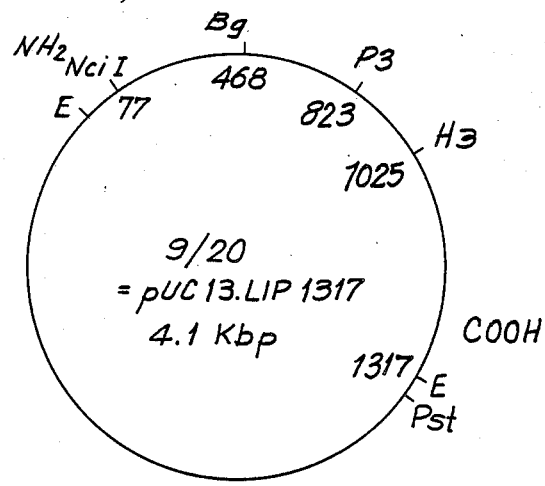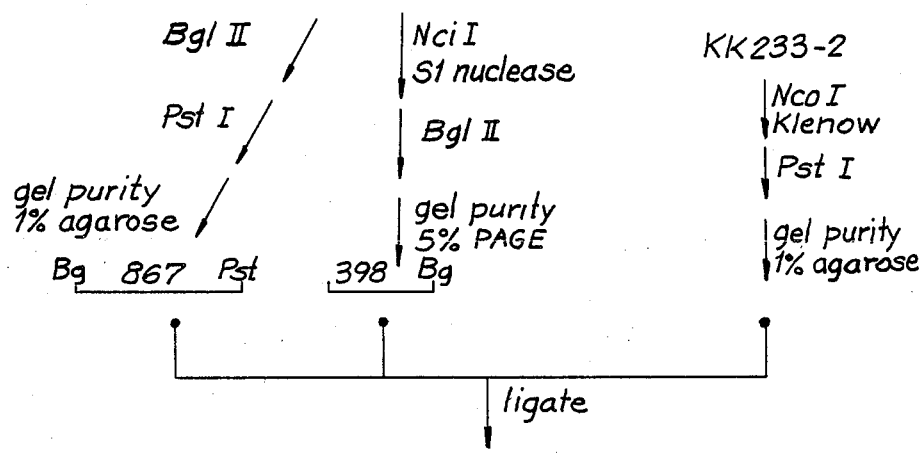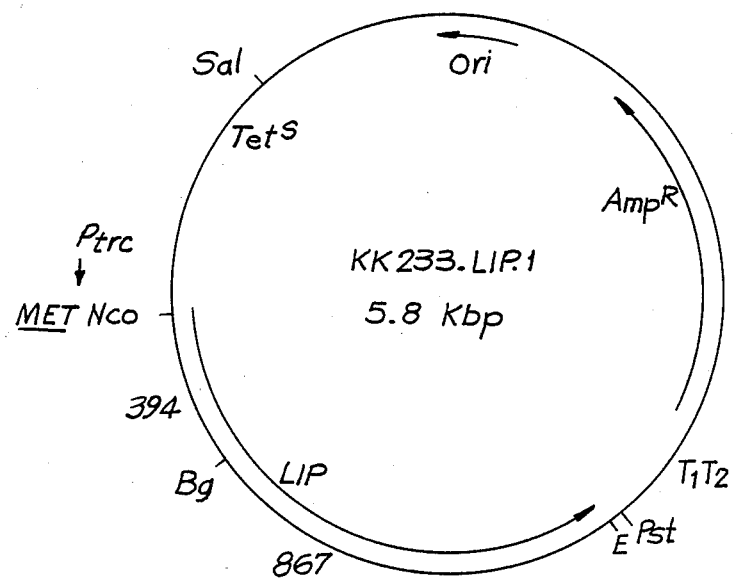
FIG. 5

DNA SEQUENCES, RECOMBINANT DNA MOLECULES AND PROCESSES FOR PRODUCING HUMAN PHOSPHOLIPASE INHIBITOR-LIKE POLYPEPTIDES

This application is a continuation-in-part of U.S. patent application Ser. No. 690,146, filed on Jan. 10, 1985 in the U.S. Patent and Trademark Office.

TECHNICAL FIELD OF THE INVENTION

This invention relates to DNA sequences, recombinant DNA molecules and processes for producing at least one human phospholipase inhibitor protein. More particularly, the invention relates to DNA sequences and recombinant DNA molecules that are characterized in that they code for at least one human phospholipase inhibitor-like polypeptide. Accordingly, hosts transformed with these sequences may be employed in the processes of this invention to produce the human phospholipase inhibitor-like polypeptides of this invention. These poypeptides possess anti-inflammatory activity and are useful in the treatment of arthritic, allergic, dermatologic, ophthalmic and collagen diseases.

BACKGROUND OF THE INVENTION

Arachidonic acid is an unsaturated fatty acid that is a precursor in the synthesis of compounds, such as prostaglandins, hydroxy-acids and leukotrines, that are involved in inflammation reactions. It is released from membrane phospholipids by phospholipase $A_2$ activity. In response to anti-inflammatory agents, such as glucocorticoids, certain cells release proteins that have been characterized in vitro by their ability to inhibit phospholipase $A_2$. Accordingly, by inhibiting arachidonic acid production, phospholipase inhibitor proteins block the synthesis of prostaglandins and other inflammatory substances, thereby reducing inflammation [F. Hirata et al., "A Phospholipase $A_2$ Inhibitory Protein In Rabbit Neutrophils Induced By Glucocorticoids", *Proc. Natl. Acad. Sci. USA*, 77, No. 5, pp. 2533-36 (1980)].

To date, several phospholipase $A_2$ inhibitory proteins have been studied. One of them—lipomodulin—has been characterized as an about 40,000 molecular weight protein that is probably degraded by proteases in the cell to two smaller active species of about 30,000 and 15,000 molecular weight [F. Hirata et al., "Identification Of Several Species Of Phospholipase Inhibitory Protein(s) By Radioimmunoassay For Lipomodulin", *Biochem. Biophys. Res. Commun.*, 109, No. 1, pp. 223-30 (1982)]. Other experimental evidence suggests that two other phospholipase $A_2$ inhibitors, macrocortin (about 15,000 molecular weight) and renocortin (two species with molecular weights of about 15,000 and 30,000 respectively) may also be cleavage products of larger inhibitory proteins such as lipomodulin J. F. Cloix et al., "Characterization And Partial Purification Of Renocortins: Two Polypeptides Formed In Renal Cells Causing The Anti-Phospholipase-like Action Of Glucocorticoids", *Br. J. Pharmac.*, 79, pp. 313-21 (1983); G. J. Blackwell et al., "Macrocortin: A Polypeptide Causing The Anti-Phospholipase Effect Of Glucocorticoids", *Nature*, 287, pp. 147-49 (1980)].

Although lipomodulin has been isolated from rabbit neutrophil cells, macrocortin from rat macrophages and renocortin from rat renomedullary interstitial cells, the three proteins exhibit similar biological activities, molecular weights and cross-reactivity with monoclonal antibodies against lipomodulin or macrocortin. Moreover, all are induced by glucocorticoids. Thus, it has been suggested that these phospholipase inhibitory proteins are closely related to each other and are produced by cells as a general physiological mechanism of steroid action [B. Rothhut et al., "Further Characterization Of The Glucocorticoid-lnduced Antiphospholipase Protein 'Renocortin'", *Biochem. Biophys. Res. Commun.*, 117, No. 3, pp. 878-84 (1983)].

Recent data have also indicated that the 15,000 molecular weight species of lipomodulin is produced by lymphocytes in response to immunogens and acts as a glycosylation-inhibiting factor, inhibiting the glycosylation of IgE-binding factors and leading to the suppression of the IgE response [T. Uede et al., "Modulation Of The Biologic Activities Of IgE-Binding Factors: I. Identification of Glycosylation-Inhibitory Factor as a Fragment of Lipomodulin", *J. Immunol.*, 130, No. 2, pp. 878-84 (1983)].

As a result of their anti-inflammatory activities, phospholipase inhibitor proteins are useful for the treatment of disorders involving inflammatory processes. Such disorders include arthritic, allergic, dermatologic, ophthalmic and collagen diseases. Furthermore, the use of these proteins to treat inflammation might avoid the disadvantages now associated with present anti-inflammatory compounds.

At present two classes of compounds are being used for anti-inflammatory therapy: corticosteroids and nonsteroidal anti-inflammatory drugs. Corticosteroids are generally disfavored due to the severe side effects that may be associated with their use. These effects include hypertension, gastrointestinal bleeding, muscle weakness, cataracts and convulsions. Thus, nonsteroidal anti-inflammatory compounds are preferred. However, these non-steroids may also produce side effects, such as adverse effects on gastric and platelet physiology and on the central nervous system and hematopoesis. In addition, most non-steroidal anti-inflammatory agents inhibit the production of inflammatory substances via their effect on only one of the two pathways for production of those substances, i.e., either the cyclooxygenase pathway or the lipoxygenase pathway.

In contrast, phospholipase inhibitor proteins inhibit the production of inflammatory substances via both pathways. Furthermore, because phospholipase inhibitor proteins are only mediators of steroid action, it is unlikely that they will produce the side effects often associated with the use of corticosteroids. And because these inhibitor proteins are natural mediators produced by the cell, they are unlikely to have the side effects usually associated with many non-steroid anti-inflammatories.

To date, however, human phospholipase inhibitor proteins have not been purified from cells. Furthermore, even if a procedure could be developed for the purification of phospholipase inhibitors, it is doubtful that sufficient quantities of them could be produced for their many clinical and commercial applications. Accordingly, processes enabling the production of human phospholipase inhibitor proteins in clinically useful amounts would be highly advantageous in anti-inflammatory therapy.

SUMMARY OF THE INVENTION

The present invention solves the problems referred to above by providing DNA sequences coding for at least one human phospholipase inhibitor-like polypeptide and processes for producing such polypeptides in hosts transformed with those DNA sequences.

The DNA sequences of this invention are selected from the group consisting of the cDNA insert of λLC, DNA sequences which hybridize to that cDNA insert and which code on expression for a human phospholipase inhibitor-like polypeptide, and DNA sequences which code on expression for a polypeptide coded for on expression by any of the foregoing DNA sequences. Recombinant DNA molecules containing these DNA sequences, hosts transformed with them and human phospholipase inhibitor-like polypeptides coded for on expression by them are also part of this invention.

The DNA sequences, recombinant DNA molecules, hosts and processes of this invention enable the production of human phospholipase inhibitor-like polypeptides for use in the treatment of arthritic, allergic, dermatologic, ophthalmic and collagen diseases, as well as other diseases, involving inflammation processes.

BRIEF DESCRIPTION OF THE DRAWINGS

FIG. 1 depicts the amino acid sequences of fragments obtained from a cyanogen bromide digestion of rat phospholipase $A_2$ inhibitor protein.

FIG. 2 depicts the amino acid sequences of fragments obtained from tryptic digestion of rat phospholipase $A_2$ inhibitor protein.

FIG. 3 shows the four pools of chemically synthesized oligonucleotide DNA probes of the invention.

FIG. 4 displays the nucleotide sequence of the cDNA insert of λLC.

FIG. 5 depicts in schematic outline the construction of plasmid pKK233.LIP.1 used to express in one embodiment the DNA sequences of the invention.

DETAILED DESCRIPTION OF THE INVENTION

Figure 6:
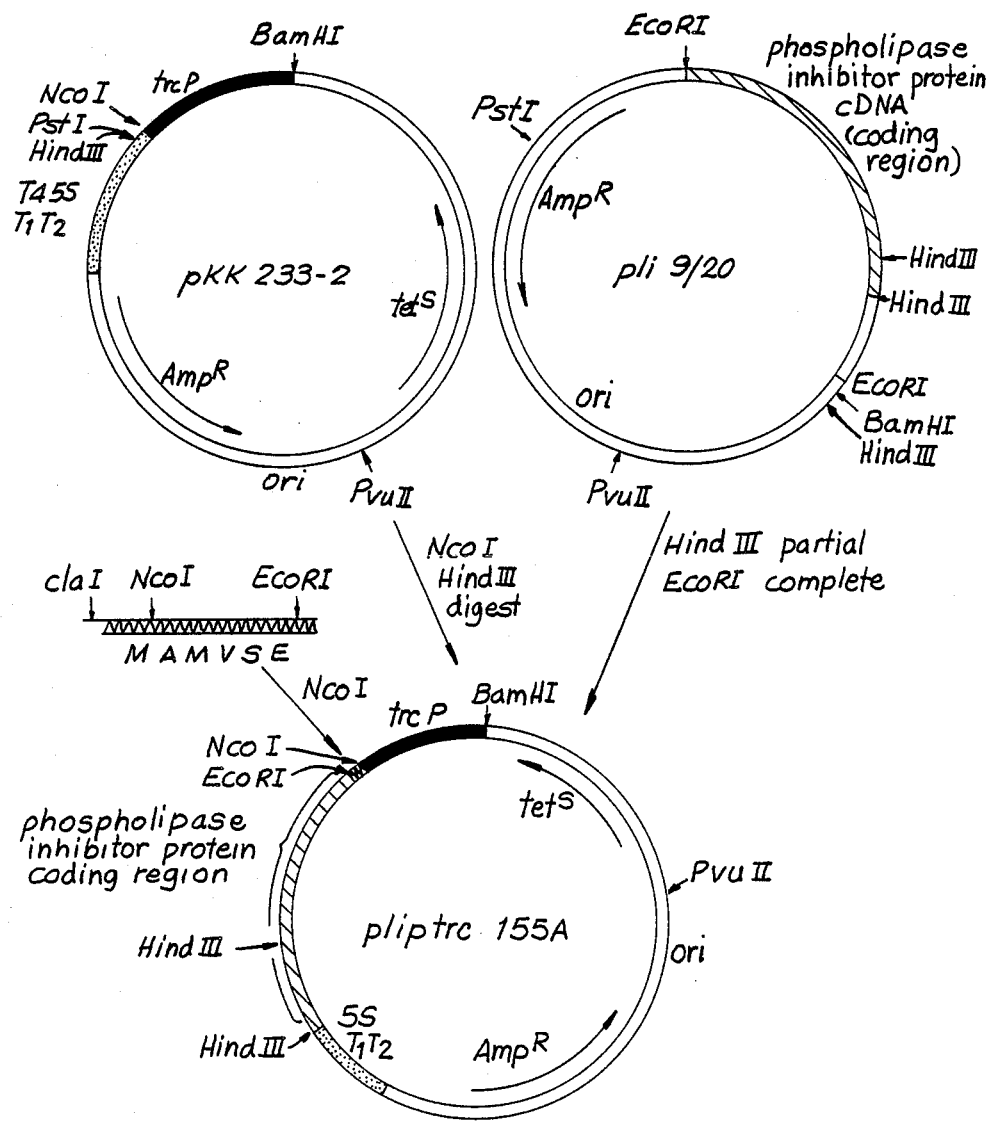
FIG. 6 depicts in schematic outline the construction of plasmid pLiptrc155A used to express in one embodiment the DNA sequences of the invention.

In order that the invention herein described may be more fully understood, the following detailed description is set forth.

In the description the following terms are employed:

Nucleotide—A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is called a nucleoside. The base characterizes the nucleotide. The four DNA bases are adenine ("A"), guanine ("G"), cytosine ("C"), and thymine ("T"). The four RNA bases are A, G, C, and uracil ("U").

DNA Sequence—A linear array of nucleotides connected one to the other by phosphodiester bonds between the 3' and 5' carbons of adjacent pentoses.

Codon—A DNA sequence of three nucleotides (a triplet) which encodes through mRNA an amino acid, a translation start signal or a translation termination signal. For example, the nucleotide triplets TTA, TTG, CTT, CTC, CTA and CTG encode for the amino acid leucine ("Leu"), TAG, TAA and TGA are translation stop signals and ATG is a translation start signal.

Reading Frame—The grouping of codons during the translation of mRNA into amino acid sequences. During translation the proper reading frame must be maintained. For example, the DNA sequence GCTGGTTGTAAG may be expressed in three reading frames or phases, each of which affords a different amino acid sequence:

GCT GGT TGT AAG—Ala-Gly-Cys-Lys
G CTG GTT GTA AG—Leu-Val-Val
GC TGG TTG TAA G—Trp-Leu-(STOP)

Polypeptide—A linear array of amino acids connected one to the other by peptide bonds between the α-amino and carboxy groups of adjacent amino acids.

Genome—The entire DNA of a cell or a virus. It includes inter alia the structural gene coding for the polypeptides of the substance, as well as operator, promoter and ribosome binding and interaction sequences, including sequences such as the Shine-Dalgarno sequences.

Gene—A DNA sequence which encodes through its template or messenger RNA ("mRNA") a sequence of amino acids characteristic of a specific polypeptide.

Transcription—The process of producing mRNA from a gene or DNA sequence.

Translation—The process of producing a polypeptide from mRNA.

Expression—The process undergone by a gene or DNA sequence to produce a polypeptide. It is a combination of transcription and translation.

Plasmid—A nonchromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. For example, a plasmid carrying the gene for tetracycline resistance (TET$^R$) transforms a cell previously sensitive to tetracycline into one which is resistant to it. A cell transformed by a plasmid is called a "transformant".

Phage or Bacteriophage—Bacterial virus many of which consist of DNA sequences encapsidated in a protein envelope or coat ("capsid").

Cosmid—A plasmid containing the cohesive end ("cos") site of bacteriophage λ. Cosmids may, because of the presence of the cos site, be packaged into λ coat protein and used to infect an appropriate host. Because of their capacity for large fragments of foreign DNA, cosmids are useful as cloning vehicles.

Cloning Vehicle—A plasmid, phage DNA, cosmid or other DNA sequence which is able to replicate in a host cell, characterized by one or a small number of endonuclease recognition sites at which such DNA sequences may be cut in a determinable fashion without attendant loss of an essential biological function of the DNA, e.g., replication, production of coat proteins or loss of promoter or binding sites, and which contain a marker suitable for use in the identification of transformed cells, e.g., tetracycline resistance or ampicillin resistance. A cloning vehicle is often called a vector.

Cloning—The process of obtaining a population of organisms or DNA sequences derived from one such organism or sequence by asexual reproduction.

Recombinant DNA Molecule or Hybrid DNA—A molecule consisting of segments of DNA from different genomes which have been joined end-to-end outside of living cells and able to be maintained in living cells.

Expression Control Sequence—A sequence of nucleotides that controls and regulates expression of genes when operatively linked to those genes.

They include the lac system, the β-lactamase system, the trp system, the tac and trc systems, the major operator and promoter regions of phage λ, the control region of fd coat protein, the early and late promoters of SV40, promoters derived from polyoma virus and adenovirus, metallothionine promoters, the promoter for 3-phosphoglycerate kinase or other glycolytic enzymes, the promoters of acid phosphatase, e.g., Pho5, the promoters of the yeast α-mating factors, and other sequences known to control the expression of genes of prokaryotic or eukaryotic cells and their viruses or combinations thereof. For mammalian cells the gene can be linked to a eukaryotic promoter such as that for the SV40 early region coupled to the gene encoding dihydrofolate reductase and selectively amplified in Chinese hamster ovary cells to produce a cell line containing many copies of actively transcribed eukaryotic genes.

Phospholipase Inhibitor-Like Polypeptide—A polypeptide displaying a biological or immunological activity of a phospholipase inhibitor protein. This polypeptide may include amino acids in addition to those of a native phospholipase inhibitor protein or it may not include all of the amino acids of native phospholipase inhibitor protein. Finally, it may include an N-terminal methionine.

The present invention relates to DNA sequences and recombinant DNA molecules coding for human phospholipase inhibitor-like polypeptides and processes for the production of those polypeptides.

Although a variety of selection and DNA cloning techniques might potentially have been employed in our isolating and cloning of a DNA sequence of this invention, we adopted a selection strategy based upon rat phospholipase $A_2$ inhibitor protein. Accordingly, we purified a rat phospholipase $A_2$ inhibitor protein from the extracellular supernatant of rat peritoneal exudate cells and determined the amino acid sequence of various fragments of that protein. Based on those protein sequences, we then synthesized several antisense oligonucleotide DNA probes corresponding to those regions of purified rat protein which had minimal nuceotide degeneracy. We then used these probes to screen a human cDNA library comprising $E.coli$ cells containing human macrophage cDNA sequences inserted into a phage cloning vector.

For screening, we hybridized the oligonucleotide probes to the human cDNA library utilizing a plaque hybridization screening assay and we selected clones hybridizing to a number of our probes. After isolating and subcloning the selected human cDNA inserts into plasmids, we determined their nucleotide sequences and compared them to our amino acid sequences from peptides of purified rat phospholipase inhibitor protein. As a result of this comparison, we found that the nucleotide sequences of all clones isolated coded for amino acid sequences that had a marked homology to the amino acid sequences of our purified rat phospholipase inhibitor protein. (Compare FIGS. 1 and 2 with FIG. 4.) We confirmed that at least one of the clones isolated contained the full length sequence encoding human phospholipase inhibitor protein.

The cDNA sequences of this invention can be operatively-linked to expression control sequences and used in various mammalian or other eukaryotic or prokaryotic host cells to produce the human phospholipase inhibitor-like polypeptides coded for by them. For example, we have constructed high level expression vectors for the production of a 37 Kd human phospholipase inhibitor protein.

In addition, the cDNA sequences of this invention are useful as probes to screen human cDNA libraries for other sequences coding for phospholipase inhibitor-like polypeptides. The cDNA sequences of this invention are also useful as probes to screen human genomic DNA libraries to select human genomic DNA sequences coding for phospholipase inhibitor-like polypeptides. These genomic sequences, like the above cDNA sequences of this invention, are then useful to produce the phospholipase inhibitor-like polypeptides coded for by them. The genomic sequences are particularly useful in transforming mammalian cells to produce human phosphoipase inhibitor-like polypeptides.

The human phospholipase inhibitor-like polypeptides produced by the methods of this invention are useful as anti-inflammatory agents and in anti-inflammatory methods and therapies. For example, such compositions may comprise an amount of a phospholipase inhibitor-like polypeptide of this invention which is pharmaceutically effective to reduce inflammation and a pharmaceutically acceptable carrier. Such therapies generally comprise a method of treating patients in a pharmaceutically acceptable manner with those compositions.

METHODS AND MATERIALS

A wide variety of host/cloning vehicle combinations may be employed in cloning or expressing the human phospholipase inhibitor-like polypeptide DNA sequences prepared in accordance with this invention. For example, useful cloning or expression vehicles may consist of segments of chromosomal, non-chromosomal and synthetic DNA sequences, such as various known derivatives of SV40 and known bacterial plasmids, e.g., plasmids from $E.coli$ including col E1, pCR1, pBR322, pMB9 and their derivatives, wider host range plasmids, e.g., RP4, phage DNAs, e.g., the numerous derivatives of phage λ, e.g., NM 989, and other DNA phages, e.g., M13 and filamentous single-stranded DNA phages and vectors derived from combinations of plasmids and phage DNAs such as plasmids which have been modified to employ phage DNA or other expression control sequences or yeast plasmids such as the 2λ plasmid or derivatives thereof.

Within each specific cloning or expression vehicle, various sites may be selected for insertion of the human phospholipase inhibitor-like polypeptide DNA sequences of this invention. These sites are usually designated by the restriction endonuclease which cuts them and are well recognized by those of skill in the art. Various methods for inserting DNA sequences into these sites to form recombinant DNA molecules are also well known. These include, for example, dG-dC or dA-dT tailing, direct ligation, synthetic linkers, exonuclease and polymerase-linked repair reactions followed by ligation, or extension of the DNA strand with DNA polymerase and an appropriate single-stranded template followed by ligation. It is, of course, to be understood that a cloning or expression vehicle useful in this invention need not have a restriction endonuclease site for insertion of the chosen DNA fragment. Instead, the vehicle could be joined to the fragment by alternative means.

Various expression control sequences may also be chosen to effect the expression of the DNA sequences of this invention. These expression control sequences include, for example, the lac system, the β-lactamase system, the trp system, the tac system, the trc system, the major operator and promoter regions of phage λ, the control regions of fd coat protein, the promoter for 3-phosphoglycerate kinase or other glycolytic enzymes, the promoters of acid phosphatase, e.g., Pho5, the promoters of the yeast α-mating factors, promoters for mammalian cells such as the SV40 early promoter, adenovirus late promoter and metallothionine promoter, and other sequences known to control the expression of genes of prokaryotic or eukaryotic cells or their viruses and various combinations thereof. In mammalian cells, it is additionally possible to amplify the expression units by linking the gene to that for dihydrofolate reductase and applying a selection to host Chinese hamster ovary cells.

For expression of the DNA sequences of this invention, these DNA sequences are operatively-linked to one or more of the above-described expression control sequences in the expression vector. Such operative linking, which may be effected before or after the chosen human phospholipase inhibitor protein DNA sequence is inserted into a cloning vehicle, enables the expression control sequences to control and promote the expression of the DNA sequence.

The vector or expression vehicle and, in particular, the sites chosen therein for insertion of the selected DNA fragment and the expression control sequence employed in this invention, are determined by a variety of factors, e.g., number of sites susceptible to a particular restriction enzyme, size of the protein to be expressed, expression characteristics such as the location of start and stop codons relative to the vector sequences, and other factors recognized by those of skill in the art. The choice of a vector, expression control sequence, and insertion site for a particular phospholipase inhibitor protein in sequence is determined by a balance of these factors, not all selections being equally effective for a given case.

It should also be understood that the DNA sequences coding for the phospholipase inhibitor-like polypeptides of this invention which are inserted at the selected site of a cloning or expression vehicle may include nucleotides which are not part of the actual gene coding for the desired phospholipase inhibitor or may include only a fragment of the entire gene for that protein. It is only required that whatever DNA sequence is employed, a transformed host will produce a phospholipase inhibitor-like polypeptide. For example, the phospholipase inhibitor-related DNA sequences of this invention may be fused in the same reading frame in an expression vector of this invention to at least a portion of a DNA sequence coding for at least one eukaryotic or prokaryotic carrier protein or a DNA sequence coding for at least one eukaryotic or prokaryotic signal sequence, or combinations thereof. Such constructions may aid in expression of the desired phospholipase inhibitor-related DNA sequence, improve purification or permit secretion, and preferably maturation, of the phospoipase inhibitor-like polypeptide from the host cell. The phospholipase inhibitor protein-related DNA sequence may alternatively include an ATG start codon, alone or together with other codons, fused directly to the sequence encoding the first amino acid of a mature native phospholipase inhibitor-like polypeptide. Such constructions enable the reduction of, for example, a methionyl or other peptidyl-phospholipase inhibitor-like polypeptide that is part of this invention. This N-terminal methionine or peptide may then be cleaved intra- or extra-cellularly by a variety of known processes or the polypeptide used together with the methionine attached to the peptide in the anti-inflammatory compositions and methods of this invention.

The cloning vehicle or expression vector containing the phospholipase inhibitor-like polypeptide coding sequences of this invention is employed in accordance with this invention to transform an appropriate host so as to permit that host to express the phospholipase inhibitor-like polypeptide for which the DNA sequence codes.

Useful cloning or expression hosts include strains of $E.\,coli$, such as $E.\,coli$ W3110IQ, $E.\,coli$ JA$_{221}$, $E.\,coli$ C600, $E.\,coli$ ED8767, $E.\,coli$ DH1, $E.\,coli$ LE392, $E.\,coli$ HB 101, $E.\,coli$ X1776, $E.\,coli$ X2282, $E.\,coli$ MRCI, and strains of Pseudomonas, Bacillus, and Streptomyces, yeasts and other fungi, animal hosts, such as CHO cells or mouse cells, other animal (including human) hosts, plant cells in culture or other hosts.

The selection of an appropriate host is also controlled by a number of factors recognized by the art. These include, for example, compatibility with the chosen vector, toxicity of proteins encoded by the hybrid plasmid, susceptibility of the desired protein to proteolytic degradation by host cell enzymes, contamination or binding of the protein to be expressed by host cell proteins difficult to remove during purification, ease of recovery of the desired protein, expression characteristics, biosafety and cost. A balance of these factors must be struck with the understanding that not all host vector combinations may be equally effective for either the cloning or expression of a particular recombinant DNA molecule.

It should be understood that the human phospholipase inhibitor-like polypeptides (prepared in accordance with this invention in those hosts) may include polypeptides in the form of fused proteins (e.g., linked to a prokaryotic, eukaryotic or combination N-terminal segment to direct excretion, improve stability, improve purification or improve possible cleavage of the N-terminal segment), in the form of a precursor of phospholipase inhibitor-like polypeptides (e.g., starting with all or parts of a phospholipase inhibitor-like polypeptide signal sequence or other eukaryotic or prokaryotic signal sequences), in the form of a mature phospholipase inhibitor-like polypeptide, or in the form of an f-met-phospholipase inhibitor-like polypeptide.

One particularly useful form of a polypeptide in accordance with this invention, or at least a precursor thereof, is a mature phospholipase inhibitor-like polypeptide with an easily cleaved amino acid or series of amino acids attached to the amino terminus. Such construction allows synthesis of the protein in an appropriate host, where a start signal that may not be present in the mature phospholipase inhibitor is needed, and then cleavage in vivo or in vitro of the extra amino acids to produce mature phospholipase inhibitor-like polypeptides. Such methods exist in the art. See, e.g., U.S. Pat. Nos. 4,332,892, 4,338,397, and 4,425,437. The polypeptides may also be glycosylated, like some native phospholipase inhibitor proteins, unglycosylated, or have a glycosylation pattern different than that of native phospholipase inhibitor proteins. Such glycosylation will result from the choice of host cell or post-expression treatment chosen for the particular inhibitor.

The polypeptides of the invention also include phospholipase inhibitor-like polypeptides that are coded for on expression by DNA sequences characterized by different codons for some or all of the codons of the present DNA sequences. These substituted codons may code for amino acids identical to those coded for by the codons replaced but result in higher yield of the polypeptide. Alternatively, the replacement of one or a combination of codons leading to amino acid replacement or to a longer or shorter phospholipase inhibitor-like polypeptide may alter its properties in a useful way (e.g., increase the stability, increase the solubility or increase the therapeutic activity).

In order that this invention may be better understood, the following examples are set forth. These examples are for purposes of illustration only and are not to be construed as limiting the scope of the invention in any manner.

EXAMPLES

Purification of a Rat Phospholipase $A_2$ Inhibitor Protein

We injected male Wistar rats (200-250 kg) subcutaneously with 0.1 ml of the glucocorticoid, dexamethasone phosphate (1.25 mg/kg rat) in 0.9% NaCl to induce production of phospholipase $A_2$ inhibitor protein. We then sacrificed the rats one hour after injection by intracardiac injection with Euthasate and washed the peritoneal cavities with 10 ml of phosphate buffered saline (50 mM $KH_2PO_4$, pH 7.3, 150 mM NaCl containing 2 U/ml heparin and 50 $\mu$M phenylmethylsulfonylfluoride). After we cleared the lavages of cells and other particulate matter by centrifugation in an International centrifuge at top speed for 30 min, we assayed the combined supernatants for phospholipase inhibitor protein by measuring the inhibition of release of labeled oleic acid from autoclaved E.coli membranes in the presence of the supernatant and porcine pantreatic phospholipase $A_2$.

We performed this in vitro assay as follows: We mixed 200 $\mu$l samples from the peritoneal exudate supernatant in 1.5 ml Eppendorf tubes with 50 $\mu$l of 0.7M Tris-HCl (pH 8.0), 60 mM $CaCl_2$ buffer on ice. We then added 50 $\mu$l of diluted porcine pancreatic phospholipase $A_2$ (Catalogue no. P9139, Sigma Chemicals) and mixed and incubated the solutions on ice for 1 h. Dilutions of the phospholipase $A_2$ suspension into buffer (70 mM Tris-HCl (pH 8.0), 6 mM $CaCl_2$) containing 2.5 mg/ml bovine serum albumin (BSA) were such that the final concentrations of phospholipase and BSA were 100 ng/50 $\mu$l and 125 $\mu$g/50 $\mu$l, respectively. We then added 25 $\mu$l of autoclaved $^3$H-oleic acid-labeled E.coli as substrate and incubated the mixtures at 6° C. for 8 min (both the temperature and length of incubation must be determined for each batch of E.coli utilized).

We prepared the substrate $^3$H-oleic acid-labeled E.coli as follows: We grew an overnight culture of E.coli in tryptone medium (1% bactotryptone, 0.5% NaCl), diluted it 1:20 with fresh broth and monitored cell growth with a Klett meter. At a reading of 40 (i.e., when cells were growing well), we added a 1:100 dilution of Brij 35 (polyoxyethylene-23-ether, Sigma Chemicals, 10% solution in water) and a 1:200 dilution of $^3$H-oleic acid (9,10-$^3$H-[N]-oleic acid, New England Nuclear) at 10 mCi/ml. After 5 h, when cell growth leveled off, we autoclaved the suspension for 20 min at 120° C. and stored the flask overnight at 4° C. We then pelleted the bacteria by centrifugation for 30 min at 16,000 rpm in an SS34 rotor at 4° C. and combined the loose pellets into a single tube. We washed the bacteria four times, or until counts in the supernatant were low, with suspension buffer (0.7M Tris-HCl (pH 8.0) 10 mM $CaCl_2$) plus 0.1% BSA. We stored the bacteria at 4° C. in suspension buffer containing 0.2% sodium azide. Typically, we prepared a 400 ml culture labeled with 20 mCi of $^3$H-oleic acid. This yielded about $7 \times 10^8$ cpm or about 10% of the input counts in labeled bacteria. For each point in an assay, we used 100,000 cpm, which was added in a volume of 25 $\mu$l. Immediately prior to use, we washed our aliquots first in 200 mM Tris-HCl (pH 8.0), 12 mM EDTA (left on ice 30 min) and then in 25 mM Tris-HCl (pH 8.0).

After the brief incubation of substrate (autoclaved labeled E.coli) with inhibitor plus phospholipase $A_2$, the reaction was stopped immediately by adding 100 $\mu$l of 2N HCl to each tube followed by the addition of 100 $\mu$l of 20 mg/ml delipidated BSA (99% albumin, Sigma Chemicas). Tubes were vortexed and incubated on ice for 30 min. The latter step was crucial for extracting the lipase digestion products from the particulate membranes.

We then pelleted the E.coli in an Eppendorf centrifuge for 5 min at 10,000 g and counted 250 $\mu$l of each supernatant in 4 ml of a scintillation cocktail compatible with aqueous solutions. In this assay, we tested each sample in duplicate using an internal control in which the sample plus E.coli substrate was incubated both in the presence and absence of added phospholipase. This in vitro assay demonstrated that our peritoneal exudates contained phospholipase inhibitory activity.

To purify the phospholipase inhibitor protein from the above-described peritoneal exudate supernatant, we first added additional protease inhibitors to the supernatant. These typically included aprotinin (20 $\mu$g/ml), soybean trypsin inhibitor (20 $\mu$g/ml) and EGTA (ethyleneglycol-bis(aminoethyl ether) N,N'-tetraacetic acid) (0.5 mM). We incubated the exudate at 37° C. for 1 h in the presence of 0.1 U/ml calf intestinal alkaline phosphatase and concentrated it two-fold by ultrafiltration to a final protein concentration of 5 mg/ml using an Amicon apparatus (PM10 membrane). We next dialyzed the supernatant overnight at 4° C. against 40 volumes of 20 mM Tris-HCl (pH 8.1) and subjected it to DE52 ion exchange column chromatography (Whatman Ltd., column dimensions: 1 cm dia. $\times$ 17 cm). Prior to use, we had equilibrated the DE52 resin with 25 mM Tris-HCl (pH 8.1). We collected the flow-through fractions and concentrated them an additional 25-fold by Amicon ultrafiltration (PM10 membrane). We then subjected the concentrate to a gel filtration column (P150 resin) in 25 mM Tris-HCl (column dimensions: 2.5 cm dia. $\times$ 40 cm) and monitored the column fractions for protein using absorbance at 280 nm and using the phospholipase inhibitory activity assay described above. We detected peak activity at 35-40,000 molecular weight.

We lyophilized these high activity fractions, dialyzed them against 25 mM Tris-HCl (pH 6.8) containing 0.2% SDS and analyzed them using a preparative SDS-polyacrylamide gel (main gel: 15% acrylamide, 0.08% methylene bisacrylamide; stacking gel: 7.6% acrylamide, 0.21% methylene bisacrylamide). The gel analysis yielded four major protein bands. According to a modification of the Western blotting technique [H. Towbin et al., "Electrophoretic Transfer Of Proteins From Polyacrylamide Gels To Nitrocellulose Sheets", *Proc.*

*Natl. Acad. Sci. USA*, 76, pp. 4350-54 (1979)] using a horse radish peroxidase antibody conjugate to visualize the immunoreactive species, we found that only one of the four major bands cross reacted with a neutralizing antibody which we prepared against a snake venom phospholipase inhibitory protein. Accordingly, we excised this region of the gel, electroeluted and precipitated the contained protein from it with 20% trichloroacetic acid and pelleted the protein by centrifugation for 20 min at 10,000 g. After washing the pellets twice with 5 ml of −20° C. acetone, each washing being followed by a centrifugation step, we dried the pellets under vacuum.

We then digested the protein either with cyanogen bromide or with trypsin. When utilizing cyanogen bromide digestion, we digested the pellets containing approximately 100 μg protein with 200 mg/ml of cyanogen bromide in the dark for 16 h at 25° C. in 0.5 ml of 70% formic acid. We then diluted the reaction mixture 15-fold with water and lyophilized it. When utilizing tryptic digestion, we first resuspended the pellets in 0.1M $NH_4HCO_3$ plus 0.1 mM $CaCl_2$, carboxymethylated the mixture with iodoacetic acid and then incubated it with trypsin for 24 h at 37° C. During this incubation, we added trypsin three times to a final concentration of 1.5% of total protein at time zero, 2.5% after 4 h and 3.5% after 19 h.

We resolved the cleavage fragments from these digestions by high pressure liquid chromatography using a C8 column (Brownlee RP-3) for the cyanogen bromide digestion products and using a C18 column (Spectraphysics) for the tryptic digestion products, utilizing in both cases a gradient of acetonitrile from 0-75% in 0.1% trifluoroacetic acid to elute bound fragments. We then subjected the peak fractions to sequence analysis using a gas phase sequencer (Applied Biosystems 470A). PITH-amino acids were analyzed by high pressure liquid chromatography on a 5 μm cyanocolumn (Hypersil), using a gradient of acetonitrile:methanol (4:1) from 15-55% in 0.02M sodium acetate (pH 5.7).

FIG. 1 shows the amino acid sequences of the fragments produced by cyanogen bromide digestion of our purified rat phospholipase inhibitor protein. Of six major peaks, only three yielded unique sequences (CNBr 1, 2 and 3). These sequences are shown at the bottom of FIG. 1. Of the remaining peaks, two (CNBr 5 and 6) contained mixtures of fragments and thus could not be sequenced, and peak 4 was a column artifact from which no protein was detected.

FIG. 2 shows the amino acid sequences of fragments from tryptic digestion. Although tryptic digestion produced over forty peaks, the amino acid sequences of only nine fractions are shown in FIG. 2. In instances where peaks contained more than one peptide, the appropriate fractions were subjected to a second chromatography step. T22a and T22b are sequences derived from the two components of peak 22 which were resolved when peak 22 was rechromatographed on the same column but at a neutral pH.

Thesis of Oligonucleotide DNA Probes for Phospholipase Inhibitor Protein Sequences Having determined the amino acid sequences of various regions of a rat phospholipase inhibitor protein (see FIGS. 1 and 2), we chemically synthesized four pools of antisense oligonucleotide DNA probes that coded for some of those protein sequences (see FIG. 3). We decided to synthesize the four pools shown in FIG. 3 because they corresponded to regions of the rat phospholipase inhibitor protein that have minimal nucleic acid degeneracy. For each amino acid sequence, we synthesized mixtures of probes complementary to all possible codons. Furthermore, we synthesized the probes such that they were complementary to the DNA sequences which code for the amino acid sequence, i.e., the probes were antisense, to enable the probes to recognize the corresponding sequences in mRNA as well as in DNA. The amino acid sequences of the four selected regions of the rat phospholipase inhibitor protein and all the possible nucleotide codon combinations that encode them are shown in FIG. 3. Coding degeneracies are indicated as follows: N=C, T, A, or G; R=A or G; Y=C or T; and H=A, C, or T.

Two pools of the probes, derived from sequences in the tryptic fragments T22a and T24 of FIG. 2, are 20-mers with 48 and 256 fold degeneracies, respectively. The other two probe pools are 17-mers with 64 and 128 fold degeneracies. To reduce further the degeneracies in the probes, we also prepared each pool in subpools, e.g., we prepared the 48 fold degenerate 20-mer of T22a in three subpools of 16 and synthesized the other probes in four subpools. The probes in each pool were end-labeled with $^{32}P$ using [γ]-$^{32}P$-ATP and T4 polynucleotide kinase.

To test if our synthetic probes actually recognized human sequences, we hybridized the four subpools of T24 to GeneScreen filters containing poly (A)+ mRNA from the human macrophage cell line U937, which had been induced with $10^{-7}$M $PMA_4\beta$-phorbol 12β myristate 13α-acetate] and $10^{-5}$ dexamethasone, utilizing the Northern blotting technique [H. Lehrach et al., *Biochemistry*, 10, pp. 4743-51 (1977)]. Subpools 2 and 3 of T24 hybridized to the mRNA and were detected as an 1800 base pair band upon autoradiography.

C. Construction and Screening of a Human cDNA Library

We constructed a human cDNA library from poly (A)+ mRNA isolated from human macrophage cell line U937. The cDNA sequences were inserted into λgt10 and amplified in *E.coli* C600 half cells.

1. Extraction of RNA from Human U937 Cells

We induced human macrophage U937 cells in culture with dexamethasone ($10^{-5}$M) and phorbol ester ($10^{-7}$M) and resuspended pellets containing $1.2 \times 10^9$ cells in 48 ml lysis buffer (0.2M Tris-HCl (pH 8.0), 0.1M LiCl, 25 mM EDTA, 1% SDS) plus 5 mM vanadyl complex (Bethesda Research Labs) by vortexing. We lysed the cells by addition of 24 ml phenol and vortexed for 5 min. We added 24 ml chloroform to the lysis mixture which was then shaken for 0 min. We separated the organic and aqueous phases by centrifugation in a clinical centrifuge at room temperature for 10 min. We reextracted the aqueous phase two times with phenol:-chloroform (1:1), then two times with chloroform only. We next ethanol-precipitated the nucleic acids in 0.3M sodium acetate at −20° C. overnight and pelleted the nucleic acid at 14k rpm in a Sorvall RC2B centrifuge (SS34 rotor) at 4° C. for 20 min. We resuspended the pellets in 5 ml 0.3M sodium acetate, and ethanol-precipitated the nucleic acid again as described above. We resuspended the final pellet in 300 μl $H_2O$ and stored it at −20° C. This RNA preparation was enriched for poly(A)+ RNA by passage over an oligo(dT)-cellulose column (PL Biochem).

2. Construction of a U937 cDNA-λgt10 Library cDNA Synthesis

We synthesized cDNA from 20 μg poly (A)+ mRNA isolated as described above. We diluted the poly (A)+ mRNA to 500 μg/ml in H$_2$O, heated it to 65° C. for 3 min, quick cooled it in a dry ice-propanol bath and then thawed it. The RNA was then added to a reaction mixture composed of 0.1M Tris-HCl (pH 8.3) at 42° C., 0.01M MgCl$_2$, 0.01M DTT, 1 mM dCTP, 1 mM dGTP, 1 mM dTTP, 0.5 mM dATP and 100 μCi α-ATP$^{32}$ (3000 Ci/mmole, Amersham or New England Nuclear), 20 μg oligo (dT)$_{12-18}$ (PL Biochem), 0.03M β-mercaptoethanol, 5 mM Vanadyl Ribonucleoside Complex (Bethesda Research Labs), 169 U AMV Reverse Transcriptase (Seikagaku America). Final volume of the reaction mixture was 200 μl. We incubated this mixture for 2 min at room temperature and 6 h at 44° C. We terminated the reaction by addition of 1/10 vol 0.5M Na$_2$EDTA (pH 8.0).

We adjusted the reaction mixture to 0.15M NaOH and incubated the mixture at 37° C. for 12 h followed by neutralization with 1/10 vol 1M Tris-HCl (pH 8.0) and HCl. This was extracted with phenol: chloroform saturated TE buffer (10 mM Tris-HCl (pH 7.0) and 1 mM Na$_2$EDTA). The aqueous phase was chromatographed through a 5 ml sterile plastic pipet containing a 7×29 cm bed of Sephadex G150 in 0.01M (pH 7.4), 0.4M NaCl, 0.01M Na$_2$EDTA, 0.05% SDS. We pooled the front peak minus tail and precipitated the cDNA with 2.5 vol 95% ethanol at −20° C. This reaction yielded 1 μg of single-stranded cDNA.

Double Strand Synthesis

We resuspended the single-stranded cDNA in 200 μl (final vl) 0.1M Hepes (pH 6.9), 0.01M MgCl$_2$, 0.0025M DTT, 0.07M KCl, 1 mM dXTPs and 75 U Klenow fragment DNA polymerase 1 (Boehringer-Mannheim) and incubated the reaction mixture at 14° C. for 21 h. Reaction was terminated by addition of Na$_2$EDTA (pH 8.0) to 0.0125M, extracted with phenol:chloroform, as in the first cDNA step, and the aqueous phase was chromatographed on a G150 column in 0.01M Tris-HCl (pH 7.4), 0.1M NaCl, 0.01M Na$_2$EDTA, 0.05% SDS. We again pooled the radioactive peak minus the tail and ethanol-precipitated the DNA.

We then incubated the DNA obtained with 42 U reverse transcriptase in 50 μl 1 0.1M Tris-HCl (pH 8.3), 0.01M MgCl$_2$, 0.01M DDT, 0.1M KCl, 1 mM dXTPS, 0.03M β-mercaptoethanol for 1 h at 37° C. to complete double-strand synthesis. The reaction was terminated and processed as described above.

We cleaved the hairpin loop formed during double strand synthesis as follows: We redissolved the pellet in 50 μl 0.03M sodium acetate (pH 4.5), 0.3M NaCl, 0.003M ZnCl$_2$ and treated it with 100 U S$_1$ nuclease (Sigma) for 30 min at room temperature. Reaction was terminated by addition of EDTA and processed as described above. The yield after S$_1$ treatment was 900 ng dsDNA.

To assure blunt ends following S$_1$ nuclease digestion, we treated the DNA with Klenow in 0.01M Tris-HCl (pH 7.4), 0.01M MgCl$_2$, 1 mM DTT, 0.05M NaCl, 80 μM dXTP and 12.5 U Klenow in 60 μl for 90 min at 14° C., extracted with 50:50 phenol:chloroform, and chromatographed the DNA on a G50 spin column (1 ml syringe) in 0.01M Tris-HCl (pH 7.4), 0.1M NaCl, 0.01M EDTA, 0.05% SDS.

We next methylated the dsDNA by treating the DNA with EcoRI methylase in 30 μl final vol 0.1M Tris-HCl (pH 8.0), 0.01M Na$_2$EDTA, 24 μg BSA, 0.005M DTT, 30 μM S-adenosylmethionine and 5 U EcoRI Methylase for 20 min at 37° C. The reaction was heated to 70° C. for 10 min, cooled, extracted with 0:50 phenol:chloroform and chromatographed on a G50 spin column as described above.

We ligated the 900 ng cDNA to phosphorylated EcoRI linkers (New England Biolabs) using the following conditions: 0.05M Tris-HCl (pH 7.8), 0.01M MgCl$_2$, 0.02M DTT, 1 mM ATP, 50 μg/ml BSA, 0.5 μg linker, 300 U T4 DNA ligase in 7.5 μl final volume for 32 h at 14° C.

We adjusted the reaction to 0.1M Tris-HCl (pH 7.5), 0.05M NaCl, 5 mM MgCl$_2$, 100 μg/ml BSA, 125 U EcoRI (New England Biolabs), incubated the mixture for 2 h at 37° C., extracted with 50:50 phenol: chloroform and chromatographed the DNA on a G50 spin column as described earlier.

We redissolved cDNA in 100 μl 0.01M Tris-HCl (pH 7.5), 0.1M NaCl, 1 mM EDTA and chromatographed it on a 1×50 μm Biogel A50 (BIORAD) column which had been extensively washed in the same buffer (to remove ligation inhibitors). Aliquots of fractions were run on a 1% agarose gel in TBE buffer (0.089M Tris-HCl, 0.089M boric acid and 2.5 mM Na$_2$EDTA), dried and exposed at −70° C. overnight. We pooled all fractions that were larger than 500 base pairs and ethanol-precipitated the DNA for cloning into an EcoRI-cut λgt10 cloning vector. The size fractionation column yielded 126 ng of cDNA, average size approximately 1500 bp.

Library Construction

We incubated 5 μg EcoRI-cut λgt10 with 20 ng cDNA and T4 DNA ligase buffer at 42° C. for 15 min to anneal cos sites, followed by centrifugation for 5 sec in an Eppendorf centrifuge and addition of ATP to 1 mM and 2400 U T4 DNA ligase (New England Biolabs) in a final vol of 50 μl. [See Huynh, Young and Davis, "Constructing And Screening cDNA Libraries in λgt10 And λgt11", in *DNA Cloning: A Practical Approach* (D. Glover, ed.), IRL Press (Oxford 1984)]. The ligation was incubated at 14° C. overnight. We packaged the λgt10 cDNA ligation mixture into phage particles using an Amersham packaging mix Amersham packaging protocol] and diluted with 0.5 ml SM buffer (100 mM NaCl, 10 mM MgSO$_4$, 50 mM Tris-HCl (pH 7.5) and 0.01% gelatin).

We next infected *E.coli* C600 hfl cells with these phage particles to form a cDNA library of 1×10$^7$ independent recombinants See T. Maniatis, et al., *Molecular Cloning*, p. 235 (Cold Spring Harbor 1982)].

For plating and amplification of the library, 1 ml of cells plus 250 μl packaging mix was incubated at room temperature for 15 min, diluted to 50 ml in LB plus MgSO$_4$ top agarose at 50° C. and plated on LB Mg Nunc plates. This represented a plaque density of 2×10$^5$ plate. The plates were incubated at 37° C. for approximately 8 h until plaques were nearly touching.

We flooded the plates with 50 ml of cold SM buffer (0.01M Tris-HCl (pH 7.5), 0.01M MgCl$_2$, 0.1 mM Na$_2$EDTA) and eluted on a gyro-rotary shaker overnight at 4° C. We pooled the eluants into 250 ml bottles and spun at 6k for 10 min in a Sorval GSA rotor. We treated the supernatants with an equal volume of cold 20% PEG 4000-2M NaCl in ice for 3 h and pelleted the phages by centrifugation at 4k for 30 min in an H4000 rotor in an RC-3B Sorvall centrifuge. The phage pellets were thoroughly drained, resuspended in 60 ml SM, and spun at 10,000 rpm in a SS34 rotor to remove debris. The supernatants were adjusted to 3.5M CsCl by addition of 7 g CsCl to 10 ml supernatant. We obtained phage bands by centrifugation in a 70.1 Beckman rotor at 50,000 rpm for 18 h at 15° C. We pooled the phage bands and stored them at 4° C. for library stock. The titer obtained was $2.2 \times 10^{13}$ PFU/ml.

Screening Of The Library

We screened the library with our labeled oligonucleotide probes, pools 2 and 3, for phospholipase inhibitor protein sequences using the plaque hydridization screening technique of Woo [S. L. C. Woo, "A Sensitive And Rapid Method For Recombinant Phage Screening", in *Methods In Enzymology*, 68, pp. 389-96 (Academic Press 1979)].

An overnight culture of C600 hfl cells in L broth and 0.2% maltose was pelleted and resuspended in an equal volume of SM buffer. We pre-adsorbed 0.9 ml of cells with $2 \times 10^5$ phage particles at room temperature for 15 min. We diluted the suspension to 50 ml in LB plus 10 mM MgSO$_4$ and 0.7% agarose at 55° C. and plated it on LB Mg Nunc plates. We screened 10 such plates. We incubated the plates at 37° C. for approximately 8 h until plaques were nearly touching. We then chilled the plates at 4° C. for 1 h to allow the agarose to harden. We presoaked GeneScreen Plus filters in a 1:10 dilution of the overnight *E.coli* C600 hfl cells for 10 min at room temperature so that a lawn of *E.coli* cells covered each filter. We then transferred the λ phage particles from the plaque library plates to these bacteria-coated filters as follows:

We placed the filters onto the plates containing the recombinant plaques for 5 min, and then lifted and incubated the filters with the phage-containing side up on LB+10 mM MgSO$_4$ plates at 37° C. for 5 h.

These filters were then lysed by placing them onto a pool of 0.5N NaOH for 5 min, then neutralized on 1M Tris-HCl (pH 7.0), submerged into 1M Tris-HCl (pH 7.0) and scrubbed clean of cell debris.

We prehybridized and hybridized the filters to the oligonucleotide probes 2 and 3 in 0.2% polyvinyl-pyrrolidone (M.W. 40,000), 0.2% ficoll (M.W. 40,000), 0.2% bovine serum albumin, 0.05M Tris-HCl (pH 7.5), 1M sodium chloride, 0.1% sodium pyrophosphate, 1% SDS, 10% dextran sulfate (M.W. 500,000) and denatured salmon sperm DNA (>100 μg/ml) according to manufacturer's specifications (New England Nuclear) for plaque screen membranes). We detected hybridizing λ-cDNA sequences by autoradiography.

By means of this technique, we picked 20 positive plaques and rescreened at lower density using the same probes.

We isolated the DNA of these clones, digested with EcoRI, and hybridized them with the four pools of rat phospholipase inhibitor protein probes using the Southern blot technique [E. M. Southern, "Detection Of Specific Sequences Among DNA Fragments Separated By Gel Electrophoresis", *J. Mol. Biol.*, 98, pp. 503-18 (1975)]. Two of the clones, λ9-111 and λ4-211, contained inserted cDNA which hybridized not only to the T24 probe but to the T22a and T29 probes as well.

We restricted the DNAs of these phages with EcoRI and isolated the cDNA inserts. By restricting Clone 9-111 with EcoRI we obtained a 1400 base pair fragment while restriction of Clone 4-211 gave three EcoRI fragments, 1300, 300 and 75 base pairs in length. We subcloned some of these fragments into plasmid pUC13 to produce recombinant plasmids pL9/20 (9-111), pL4/10 large (4-211, 1300 bp), and pL4/10 small (4-211, 300 bp). We then sequenced these plasmids by the method of Maxam and Gilbert [A. M. Maxam and W. Gilbert, "A New Method For Sequencing DNA", *Proc. Natl. Acad. Sci. USA*, 74, pp. 560-64 (1977)]. This sequencing analysis demonstrated that the clones contained nucleotide sequences which corresponded to the amino acid sequences of the purified rat phospholipase inhibitor protein but seemed to be lacking the most 5' sequence.

A 480 base pair EcoRI-BglII fragment of pLg/20 was used as a probe to rescreen the U937-λgt10 library. Seventy-two positives were isolated and partially plaque purified by rescreening at lower density. The DNA of each of these positives was digested with HhaI and analyzed by the Southern blotting technique [E. M. Southern, supra] using a 30 oligonucleotide sequence (lipo 16) as a probe. Lipo 16 corresponds to the sequence starting at base pair 81-111 of the sequence presented in FIG. 4. Fourteen of these clones showed a positive signal and were further analyzed by genomic sequencing [G. Church and W. Gilbert, *Proc. Natl. Acad. Sci. USA*, 81, p. 1991 (1984)] by digesting DNA with MspI and using lipo 16 as probe. Seven clones, λL110, λL106, λL112, λLC, λLH, λLN, λLDD, contained an 81 base pair sequence 5' to the lipo 16 probe sequence.

These clones contain cDNA sequences having an uninterrupted open reading frame that can code for 363 amino acids (see FIG. 4). We believe that the initiating ATG codon for phospholipase inhibitor protein may be the ATG located at nucleotides 52-54 of FIG. 4. However, the DNA sequence of our clone, reported in FIG. 4, may be lacking one or more codons coding for amino acids in the N-terminal end of native phospholipase inhibitor protein. These potential missing codons may be isolated, if necessary, by one of skill in the art using conventional hybridization conditions from our libraries, or other libraries, of genomic DNA and cDNA using as probes our clones, or more preferably portions of the 5' terminal end of those clones. Full length clones may then be prepared using conventional ligation techniques and our phospholipase inhibitor protein coding clones.

We confirmed that clone λLC of FIG. 4 contains the full length gene for human phospholipase inhibitor protein. To confirm that the ATG at nucleotides 52-54 in the λLC cDNA (FIG. 4) is the first in frame methionine codon and thus the initiating methionine, we determined the 5' sequence of the phospholipase inhibitor protein mRNA by primer extension. A 27 oligonucleotide (lipo 18) homologous to the sequence 10 to 37 of λLC was labelled with $^{32}$P-(γ)-ATP and hybridized to human placental poly (A)+ RNA. Using this oligonucleotide as a primer and AMV reverse transcriptase, we transcribed a 60 base pair fragment of the most 5' end of the phospholipase inhibitor protein mRNA. This fragment was gel purified and sequenced by the Maxam and Gilbert sequencing technique (supra). The resulting sequence showed 37 base pairs homologous to sequence 1 to 37 of λLC and 23 additional nucleotides that represented the 5' end of the phospholipase inhibitor protein mRNA.

To exclude the possibility that the mRNA was in fact longer than our primer extension indicated, but instead had a strong stop signal for reverse transcriptase which we mistook for the 5' end, we determined the exact size of the mRNA. An oligonucleotide (lipo 17) that is homologous to sequence 94 to 128 of λLC was hybridized to placental poly (A)+ RNA and digested with RNase H. RNase H digests RNA only when in a hybrid with DNA and thus it introduced a defined cleavage in the mRNA at the site where lipo 17 hybridized. This RNA was then separated on a sequencing gel, blotted onto Gene Screen and probed with $^{32}$P-labelled lipo 18. This enabled us to determine the exact size of the 5' end of the phospholipase inhibitor mRNA, which agreed with the size obtained by primer extension.

The cDNA sequences of this invention can be further utilized to screen human genomic cosmid or phage libraries to isolate human genomic sequences encoding human phospholipase inhibitor-like polypeptides.*

* For example, an EcoRI fragment of plasmid pL9/20 was used to screen a partial HaeIII-AluI human liver library (R. Lawn et al., "The Isolation and Characterization of Linked Δ and β Globin Genes From a Cloned Library of Human DNA", Cell, 15, pp. 1157-74 (1978)), and positive clones were obtained.

These human cDNA and genomic sequences can be used to transform eukaryotic and prokaryotic host cells by techniques well known in the art to produce human phospholipase inhibitor-like polypeptides in clinically and commercially useful amounts.

It should also be understood that the cDNA sequences of the invention may be contained in larger mRNA species which result from alternate splicing. Such mRNAs may encode a signal sequence for phospholipase inhibitor protein in addition to the mature protein.

Expression of a Phospholipase Inhibitor Protein in E.coli

Plasmid pKK233.LIP.1 (which contains a partial sequence of the phospholipase inhibitor protein coding region) was constructed by a three part ligation using NcoI-PstI-cut pKK233-2 [E. Amann et al., "Vectors Bearing A Hybrid Trp-Lac Promoter Useful For Regulated Expression Of Cloned Genes In *Escherichia coli*", Gene, 25, pp. 167-78 (1983)] and the BglII-PstI and NciI-BglII fragments from pL9/20 (see FIG. 5). Plasmid pL9/20 contains the DNA sequence of nucleotides 67-1376 of the cDNA insert of λLC shown in FIG. 4 inserted into the EcoRI site of pUC13.

Transformants resulting from this ligation and subsequent transformation into E.coli strain HB101 I$^Q$ were picked into microtiter wells containing L broth plus ampicillin and grown overnight. The overnight cultures were then replicated onto nitrocellulose filters on L broth agar plus ampicillin plates in quadruplicate and incubated for approximately 4 h at 37° C. The nitrocellulose filters were then transferred to L broth plates containing IPTG (10 μg/ml) and incubated for 0, 30, 60, or 120 min, followed by lysozyme-detergent treatment to lyse the colonies and finally by Western blot analysis with a cross reactive antiserum that was prepared against the rat phospholipase inhibitor protein. Transformants were also analyzed by plasmid restriction mapping. All the Western positive colonies contained plasmids carrying the predicted restriction fragments. Preparations of E.coli from the positive colonies were also analyzed by SDS polyacrylamide gel electrophoresis. With Western blot analysis of these preparations using the antibody against rat phospholipase inhibitor protein, we detected a 31,000 molecular weight truncated protein.

We have also constructed various expression vectors in E.coli for the production of the full length human phospholipase inhibitor protein. All are perfect constructs starting with the first methionine in the sequence depicted in FIG. 4. We confirmed expression by the procedure described above for the truncated protein, using an antiserum prepared against rat phospholipase inhibitor protein.

For example, FIG. 6 depicts plasmid pLiptrc155A, a trc expression vector derived from plasmid pKK233-2 E. Amann et al., supra]. pLiptrc155A has a hybrid promoter which contains the -10 region from lac and the -35 region from trp. It also contains the 5S RNA T$_1$T$_2$ terminators and the β-lactamase gene which confers ampicillin resistance.

pLiptrc155A was constructed as follows: Plasmid pKK233-2 was restricted with NcoI and HindIII, yielding a linear fragment. Plasmid pL9/20 was partially digested with HindIII and then completely digested with EcoRI and the 1090 fragment was isolated by agarose gel electrophoresis. These two fragments were then completely digested ligated in the presence of a NcoI-EcoRI linker containing the initiation ATG and the sequence coding for five amino acids 5' to the EcoRI site in the human phospholipase inhibitor protein cDNA.

The resulting pLiptrc155A expression vector was then used to transform E.coli strains JA221 and W3110I$^Q$ and expression was induced by growth of the transformed strains for 4 h in LB medium containing 1 mM IPTG and 35 μg/ml ampicillin. SDS polyacrylamide gel analysis of crude lysates of the transformed host cells showed a single new protein band at an apparent molecular weight of 37 Kd. Control extracts from the strains not transformed with pLiptrc155A, or strains transformed with the plasmid but suppressed for production of the protein, did not show this 37 Kd protein. We found, for example, that when the JA$_{221}$ host was transformed with pLiptrc155A, the 37 Kd protein accounted for as much as 2% of the total protein.

To further verify that we were expressing the human phospholipase inhibitor protein, the same lysates were also subjected to Western blot analysis using antibody raised against the rat phospholipase inhibitor protein. Only the 37 Kd protein was immunoreactive with the antibody against the rat protein. We have also shown by Western blot analysis that the natural human phospholipase inhibitor protein from U937 cells (detected by its immunoreactivity with the anti-rat protein antibody) is virtually identical in size with the 37 Kd protein we expressed, banding in the same place on the gel.

Finally, a small amount of the expressed protein was electroluted out of an SDS polyacrylamide gel and subjected to N-terminal sequence analysis. The amino acid sequence obtained was consistent with the predicted amino acid sequence of the λLC cDNA sequence of FIG. 4.

The human phospholipase inhibitor protein which we expressed inhibited exogenous phospholipase A2 in the in vitro assay described in Example A above. This inhibition was detected first using crude lysates and later with a more purified preparation of expressed protein. When the soluble fraction of crude lysates prepared with a french pressure cell was assayed for phospholipase inhibitory activity, we obtained the results shown in Table I below. Inhibitory activity was detected in E.coli lysates containing plasmid pLiptrc155A, while no activity was detected in lysates from E.coli that did not contain the plasmid. As determined by gel analysis, the only difference between these two extracts was the presence of the 37 Kd protein in the inhibitory fraction. We found that the 37 Kd protein accounted for less than 1% of the total protein in the lysate. We also obtained similar results when sonicated lysates were assayed.

Although inhibitory activity could be detected directly in the soluble lysate, most of the 37 Kd protein in E.coli was insoluble and hence removed by low speed centrifugation after the cells were lysed with the french press. The insoluble protein was extracted from particulate matter with guanidine hydrochloride, dialyzed against 1M urea, and then assayed for phospholipase inhibitory activity. The results of this assay are shown in Table II below. The dialysate contained approximately 200 U of inhibitory activity per ml (1 U inhibits 15 ng A2). To insure that this activity was the result of a protein, and not some other component in the extract such as lipid, 25 $\mu$l of the lysate used in Table II were incubated with trypsin. As shown in Table III below, the inhibitory activity was very trypsin-sensitive.

TABLE I

Phospholipase Inhibitory Activity In Crude E. coli Lysates.

Cultures of the W3110l$^Q$ strain of E. coli, which either did or did not contain the plasmid pLiptrc155A, were induced with IPTG and lysed with a french pressure cell. Particular matter was removed by centrifugation at 10,000 xg for 20 min. The soluble fraction was assayed for phospholipase inhibitory activity. The numbers shown are the averages from several assays in which 50 $\mu$l of extracts were assayed with 100 ng of porcine pancreatic phospholipase A$_2$.

| Sample | Percent Inhibition |
|---|---|
| A$_2$ alone | 0 |
| A$_2$ + E. coli, no plasmid | 0 |
| A$_2$ + E. coli containing trc plasmid | 24 |

TABLE II

Dose-Response Curve Of Partially Purified Inhibitor.

The insoluble preparation, which was recovered from JA221 cells transformed with pLiptrc155A (using the lysis treatment described above) was exposed to 6M guanidine hydrochloride in 25 mM sodium acetate (pH 6.0). Particulate matter was removed by centrifugation (100,000 xg for 1h). Extracted protein, which was highly enriched for the human 37 Kd protein, was dialyzed against 1M urea in 25 mM sodium acetate (pH 6.0) and then assayed for phospholipase A$_2$ inhibitory activity.

| $\mu$l extract assayed | Percent Inhibition |
|---|---|
| 0 | 0 |
| 3 | 12 |
| 10 | 26 |
| 30 | 58 |

TABLE III

Trypsin Sensitivity Of Inhibitor.

The partially purified preparation described in Table II was exposed to trypsin for 15 min at room temperature and then assayed with 100 ng of porcine pancreatic phospholipase A$_2$. Under the conditions used, the trypsin treatment did not alter the phospholipase A$_2$ activity. For each sample, 25 $\mu$l of inhibitor were assayed.

| Sample | Trypsin $\mu$g/ml | Percent Inhibition |
|---|---|---|
| A$_2$ alone | 0 | 0 |
| A$_2$ + inhibitor | 0 | 54 |
| A$_2$ + inhibitor | 1 | 3 |

TABLE III-continued

| A$_2$ + inhibitor | 3 | 4 |
|---|---|---|

In addition to pLiptrc155A, we constructed other high level expression vectors of this invention. For example, plasmid pLipPLT4A was constructed as follows: plasmid PPLT4HTNF, a gift from Walter Fiers, (this plasmid is identical to the plasmid deposited in the culture collection of the Deutsche Sammlung Von Mikroorganismen, in Gottingen, West Germany, on Dec. 27, 1984 under DSM No. 3175 and which was deposited within E.coli strain C600 and designated as pBR322-pL-T4-hTNF) was digested with restriction enzymes ClaI and HindIII and a linear fragment was obtained. Plasmid pL9/20 was partially digested with HindIII and then completely with EcoRI, and the 1350 bp fragment was isolated from an agarose gel. These two fragments were ligated in the presence of a ClaI-EcoRI linker containing an initiation ATG and the sequence coding for five amino acids 5' to the EcoRI site in the phospholipase inhibitor cDNA. In the resulting expression vector, the P$_L$ promoter directs the transcription of a hybrid mRNA including sequences of P$_L$, T4 and the phospholipase inhibitor mRNA. Translation of this mRNA initiates at the first ATG of the human phospholipase inhibitor protein coding sequence, resulting in a 37 Kd protein. A second tetracycline resistant plasmid pLipPLT4T was constructed by inserting the tetracycline resistance gene of pBR322 into the ScaI site of pLipPLT4A.

We transformed E.coli strains MC1061 and C600pCi 857 with pLipPLT4A and determined expression by SDS polyacrylamide electrophoresis and Western blot analysis as described above. The E.coli extracts showed a 37 Kd protein reactive with antibody to rat phospholipase inhibitor protein.

E. Expression of Human Phospholipase Inhibitor Protein in Mammalian Cells

Figure 7:
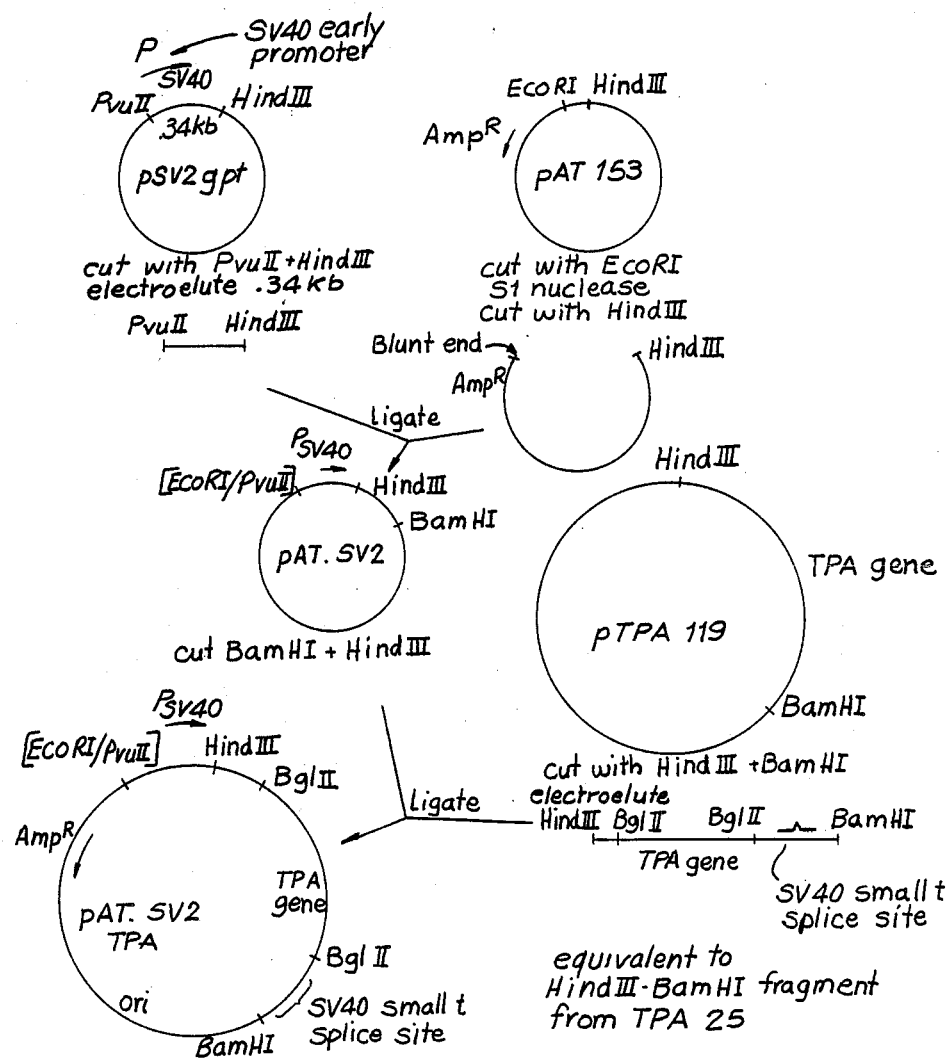
FIGS. 7-9 depict the construction of plasmid pSVL9109, a mammalian expression vector for production of human phospholipase inhibitor protein according to one embodiment of this invention.
Figure 8:
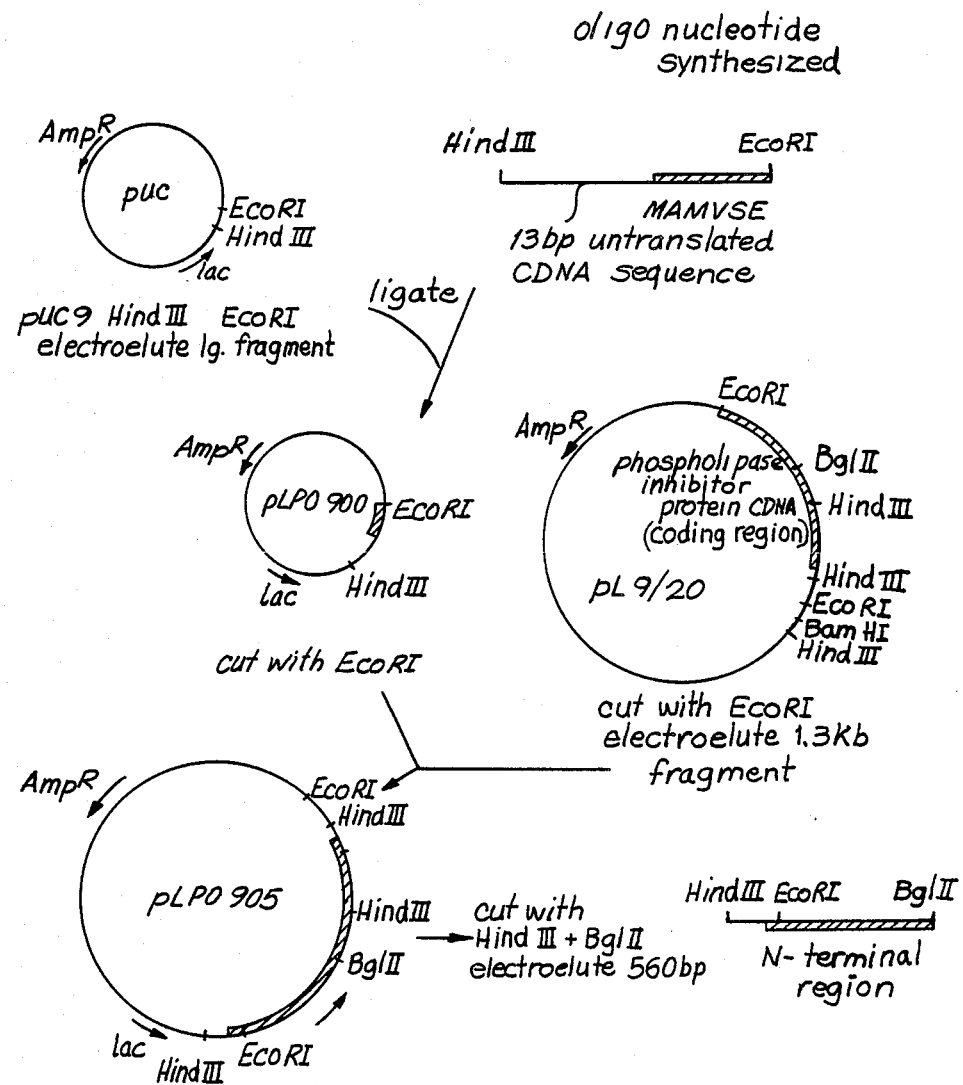
Figure 9:
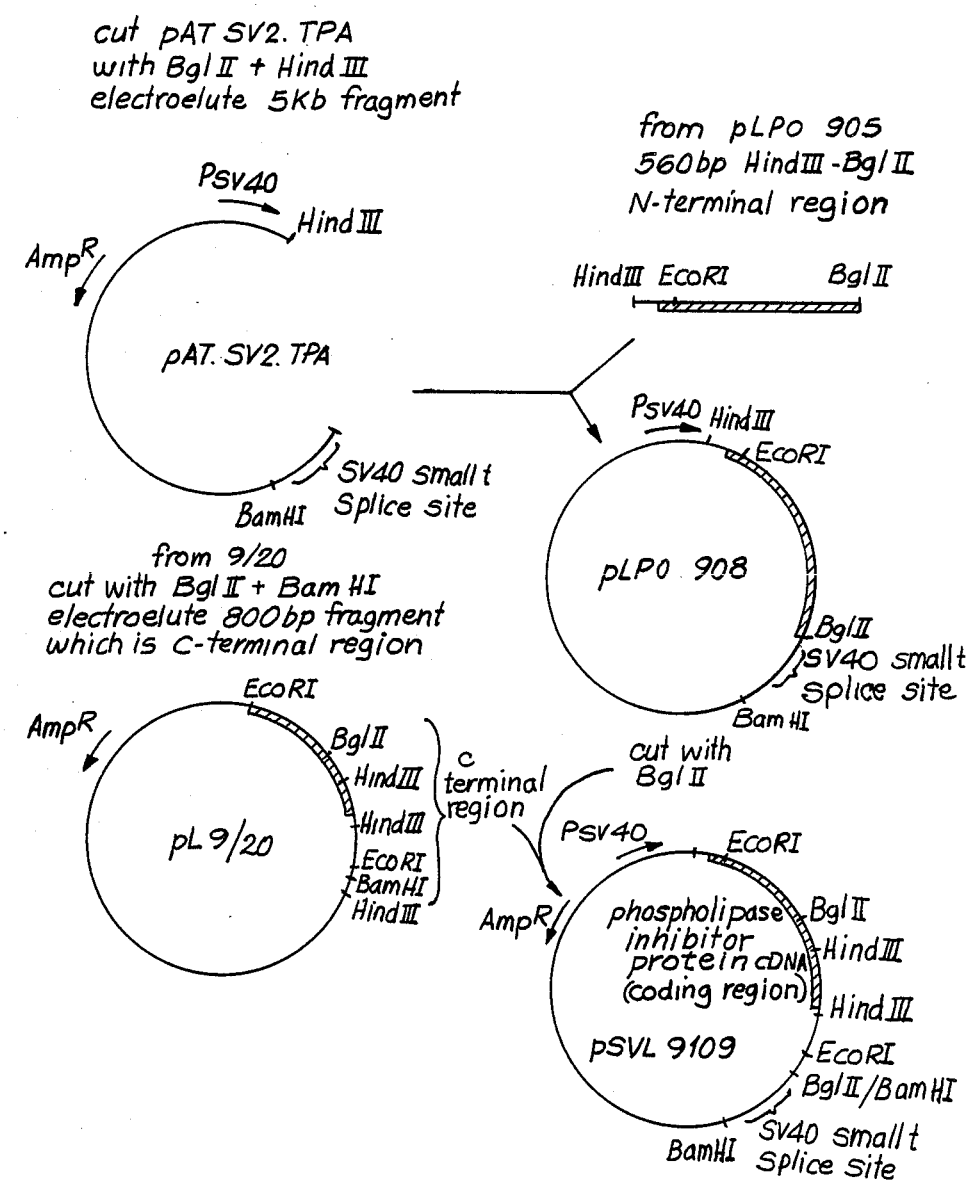

We have also constructed expression vectors for the production of human phospholipase inhibitor protein in mammalian hosts. FIGS. 7–9 show the construction of pSVL9109 which, when transfected into cos and CHO host cells by the CaPO$_4$ procedure [F. Graham et al., *J. Virology*, 52, pp. 455–56 (1973)], expressed human phospholipase inhibitor protein as detected by Western blot analysis with the anti-rat phospholipase inhibitor protein antibody. We detected a 37 Kd immunoreactive protein not observed in nontransfected cells, indicating that the vector was producing the human inhibitor protein. We constructed pSVL9109 as follows:

As shown in FIG. 7, plasmid pSV2gpt R. Mulligan et al., *Proc. Natl. Acad. Sci. USA*, 78, pp. 2072–76 (1981)] was cut with PvuII and HindIII and the 340 bp fragment containing the SV40 early promoter was isolated and inserted into pAT153 which had been previously cut with EcoRI, S1 treated, and then cut with HindIII. The resulting plasmid pAT.SV2 contained the promoter. This plasmid was then cut with HindIII and BamHI. Into this site we cloned a sequence which contained the small t splice site. This sequence was isolated from another plasmid, pTPA$_{119}$, by cutting with HindIII and BamHI. The 3 kb insert contained the DNA sequence coding for human tissue plasminogen activator along with the small t splice site. This sequence is equivalent to that found in the pTPA$_{25}$ HindIII-BamHI segment deposited with the American Type Culture Collection in Rockville, Md., on Aug. 21, 1984 under ATCC No. 39808. The HindIII-BamHI 3 kb piece was ligated to pAT.SV2 to yield plasmid pAT.SV2.TPA. This vector contains the SV40 early promoter followed by a HindIII site and the SV40 small t splice signal preceded by a BglII site.

We next inserted the coding sequence for human phospholipase inhibitor protein into pAT.SV2.TPA. An oligonucleotide of 29 bp with EcoRI and HindIII ends was synthesized (see FIG. 8). This oligonucleotide includes the coding sequence for the first six amino acids of human phospholipase inhibitor protein. This sequence was cloned into pUC9 [J. Vieira et al, *Gene*, 19, pp. 259-68 (1982)] which had been digested with EcoRI and HindIII to yield pLP0900. This plasmid was cut with EcoRI and treated with calf alkaline phosphatase. We then cloned the 1.3 kb EcoRI fragment from pL9/20 which corresponds to the coding region for human phospholipase inhibitor protein into pLP0900. The resulting plasmid pLP0905 contains the entire coding region for human phospholipase inhibitor protein with a HindIII site upstream (see FIG. 8). This makes the gene suitable for cloning behind the SV40 promoter of pAT.SV2.TPA.

FIG. 9 shows the insertion of the gene for human phospholipase inhibitor protein into pAT.SV2.TPA to form a mammalian expression vector of this invention. The human phospholipase inhibitor protein sequence was cloned into the expression vector in two parts. First, the N-terminal region was inserted behind the SV40 promoter and then the C-terminal region was added. The plasmid pLP0905 was cut with HindIII and BglII and the 560 bp fragment containing the N-terminal region of human phospholipase inhibitor protein was isolated. pAT.SV2.TPA was cut with HindIII and BglII and the 5 kb fragment containing the vector was isolated, free of TPA sequences. Into this HindIII-BglII vector, we inserted the 560 bp HindIII-BglII fragment containing the N-terminal region of human phospholipase inhibitor protein to yield the plasmid pLP0908.

The C-terminal region of human phospholipase inhibitor protein is found within the 800 bp BglII-BamHI fragment of pL9/20. Thus, pL9/20 was cut with BglII and BamHI, followed by electroelution of the 800 bp fragment. This fragment was ligated into the plasmid pLP0908 which had been cut with BglII and treated with calf alkaline phosphatase. Plasmid pSVL9109 was isolated. This plasmid has the entire human phospholipase inhibitor protein coding sequence downstream of the SV40 early promoter followed by the SV40 small t splice signal. Plasmid pSVL9109 was used to transfect cos and CHO hosts as described above.

Thus, utilizing the DNA sequences of the invention, we have constructed high level expression vectors for the expression of human phospholipase inhibitor protein in a biologically active form.

Recombinant DNA sequences prepared by the processes described herein are exemplified by a culture deposited in the culture collection of In Vitro International, Inc., Ann Arbor, Mich. The culture was deposited on Jan. 9, 1985 and is identified as follows:

λLC: IVI No. 10042

Microorganisms prepared by the processes described herein are exemplified by a culture deposited in the above-mentioned depository on Mar. 12, 1985 and identified as follows:

*E.coli* W3110I$^Q$ (pLiptrc155A): IVI No. 10046

IMPROVING THE YIELD AND ACTIVITY OF HUMAN PHOSPHOLIPASE INHIBITOR-LIKE POLYPEPTIDES PRODUCED IN ACCORDANCE WITH THIS INVENTION

The level of production of a protein is governed by three major factors: the number of copies of its gene within the cell, the efficiency with which those gene copies are transcribed and the efficiency with which they are translated. Efficiency of transcription and translation (which together comprise expression) is in turn dependent upon nucleotide sequences normally situated ahead of the desired coding sequence. These nucleotide sequences or expression control sequences define, inter alia, the location at which RNA polymerase interacts to initiate transcription (the promoter sequence) and at which ribosomes bind and interact with the mRNA (the product of transcription) to initiate translation. Not all such expression control sequences function with equal efficiency. It is thus of advantage to separate the specific phospholipase inhibitor protein coding sequences of this invention from their adjacent nucleotide sequences and to fuse them instead to other known expression control sequences so as to favor higher levels of expression and production of human phospholipase inhibitor-like polypeptides. This having been achieved, the newly engineered DNA fragments may be inserted into higher copy number plasmids or bacteriophage derivatives in order to increase the number of gene copies within the cell and thereby further to improve the yield of expressed phospholipase inhibitor-like polypeptides.

Several expression control sequences may be employed as described above. These include the operator, promoter and ribosome binding and interaction sequences (including sequences such as the Shine-Dalgarno sequences) of the lactose operon of *E.coli* ("the lac system"), the corresponding sequences of the tryptophan synthetase system of *E.coli* ("the trp system"), the major operator and promoter regions of phage λ ($O_L P_L$ as described above and $O_R P_R$), a control region of filamentous single-stranded DNA phages, the tac or trc system, the promoter for 3-phosphoglycerate kinase or other glycolytic enzymes, the promoters of acid phosphatase, e.g., Pho5, the promoters of the yeast α-mating factors, promoters for mammalian cells such as the SV40 early and late promoters, adenovirus late promoter and metallothionine promoter, and other sequences which control the expression of genes of prokaryotic or eukaryotic cells and their viruses or combinations thereof.

Therefore, to improve the production of the phospholipase inhibitor-like polypeptides of this invention, the DNA sequences for that polypeptide may be prepared as before and inserted into a recombinant DNA molecule closer to its former expression control sequence or under the control of one of the above improved expression control sequences. Such methods are known in the art.

Other methods useful to improve the efficiency of translation involve the insertion of chemically or enzymatically prepared oligonucleotides in front of the initiating codon of the phospholipase inhibitor protein-related DNA sequences of this invention or the replacement of codons at the N-terminal end of the DNA sequence with those chemically or enzymatically prepared oligonucleotides. By this procedure, a more optimal primary and higher order structure of the messenger RNA can be obtained. More specifically, a sequence can be so designed that the initiating AUG codon occurs in a readily accessible position (i.e., not masked by secondary structure) either at the top of a hairpin or in other single-stranded regions. The position and sequence of the aforementioned Shine-Dalgarno segment can similarly be optimized. The importance of the general structure (folding) of the messenger RNA has been documented [D. Iserentant and W. Fiers, "Secondary Structure Of mRNA And Efficiency Of Translation Initiation", *Gene*, 9, pp. 1-12 (1980)].

Further increases in the cellular yield of the phospholipase inhibitor-like polypeptides of this invention may be achieved by increasing the number of genes that can be utilized in the cell. This may be achieved by insertion of the phospholipase inhibitor protein gene (with or without its transcription and translation control elements) in a higher copy number plasmid or in a temperature-controlled copy number plasmid (i.e., a plasmid which carries a mutation such that the copy number of the plasmid increases after shifting the temperature B. Uhlin et al., "Plasmids With Temperature-Dependent Copy Number For Amplification Of Cloned Genes And Their Products", *Gene*, 6, pp. 91-106 (1979)].

Alternatively, an increase in gene dosage can be achieved, for example, by insertion of recombinant DNA molecules, engineered in the manner described above, into the temperate bacteriophage λ, most simply by digestion of the plasmid with a restriction enzyme, to give a linear molecule which is then mixed with a restricted phage λ cloning vehicle [e.g., of the type described by N. E. Murray et al., "Lambdoid Phages That Simplify The Recovery Of In Vitro Recombinants", *Mol. Gen. Genet.*, 150, pp. 53-61 (1977), and N. E. Murray et al., "Molecular Cloning of the DNA Ligase Gene From Bacteriophage T4", *J. Mol. Biol.*, 132, pp. 493-505 (1979)], and the recombinant DNA molecule produced by incubation with DNA ligase. The desired recombinant phage is then selected and used to lysogenize a host strain of *E.coli*.

Therefore, it should be understood that the phospholipase inhibitor-like polypeptide coding sequences of this invention may be removed from the disclosed vectors and inserted into other expression vectors, as previously described (supra) and these vectors employed in various hosts, as previously described (supra) to improve the production of the human phospholipase inhibitor-like polypeptides of this invention.

While we have hereinbefore presented a number of embodiments of this invention, it is apparent that our basic construction can be altered to provide other embodiments which utilize the processes and compositions of this invention. Therefore, it will be appreciated that the scope of this invention is to be defined by the claims appended hereto rather than by the specific embodiments which have been presented hereinbefore by way of example.

We claim:

1. A substantially pure phospholipase inhibitor, the phospholipase inhibitor:
   (a) being capable of inhibiting phospholipase $A_2$ enzymes; and
   (b) comprising the following tryptic fragments:
      (1) ser, glu, ile, asp, met, asn, glu, ile, lys;
      (2) lys, val, phe, gln, asn, atyr, arg;
      (3) thr, pro, ala, gln, phe, asp, ala, asp, glu, leu, leu, arg;
      (4) ala, ala, tyr, leu, gln, glu, thr, gly, lys, pro, leu, asp, glu, glu, thr, leu, lys; and
      (5) gly, leu, gly, thr, asp, glu;

the phospholipase inhibitor further being selected from the group consisting of:
   (a) a mature phospholipase inhibitor protein, and
   (b) an f-met-phospholipase inhibitor protein.

2. A phospholipase inhibitor produced by a unicellular host transformed with a DNA sequence selected from the group consisting of:
   (a) the cDNA insert of λLC,
   (b) TTTCTCTTTAGGTTCTTTGCAAGAAGGTAGAGATAAAGACACTTTTTCA AAAATGGCAATGGTATCAGAATTCCTCAAGCAGGCCTGGTTTATTGAAAATGAAGAG CAGGAATATGTTCAAACTGTGAAGTCATCCAAAGGTGGTCCCGGATCAGCGGTGAGC CCCTATCCTACCTTCAATCCATCCTCGGATGTCGCTGCCTTGCATAAGGCCATAATG GTTAAAGGTGTGGATGAAGCAACCATCATTGACATTCTAACTAAGCGAAACAATCCA CAGCGTCAACAGATCAAAGCAGCATATCTCCAGGAAACAGGAAAGCCCCTGGATGAA ACACTTAAGAAAGCCCTTACAGGTCACCTTGAGGAGGTTGTTATAGCTCTGCTAAAA ACTCCAGCGCAATTTGCTGCTGATGAACTTCGTGCTGCCATGAAGGGCCTTGGAACT GATGAAGATACTCTAATTGAGATTTTGGCATCAAGAACTAACAAAGAAATCAGAGAC ATTAACAGGGTCTACAGAGAGGAACTGAAGAGAGATCTGGCCAAAGACATAACCTCA GACACATCTGGAGATTTTCGGAACGCTTTGCTTTCTCTTGCTAAGGGTGACCGATCT GAGGACTTTGGTGTGAATGAAGACTTGGCTGATTCAGATGCCAGGGCCTTGTATGAA GCAGGAGAAAGGAGAAAGGGGACAGACGTAAACGTGTTCAATACCATCCTTACCACC AGAAGCTATCCACAACTTCGCAGAGTGTTTCAGAAATACACCAAGTACAGTAAGCAT GACATGAACAAAGTTCTGGACCTGGAGTTGAAAGGTGACATTGAGAAATGCCTCACA GCTATCGTGAAGTGCGCCACAAGCAAACCAGCTTTCTTTGCAGAGAAGCTTCATCAA GCCATGAAAGGTGTTGGAACTCGCCATAAGGCATTGATCAGGATTATGGTTTCCCGT TCTGAAATTGACATGAATGATATCAAAGCATTCTATCAGAAGATGTATGGTATCTCC CTTTGCCAAGCCATCCTGGATGAAACCAAAGGAGAGATTATGAGAAAATCCTGGTGGCT CTTTGTGGAGGAAACTAAACATTCCCTTGATGGTCTCAAGCTATGATCAGAAGACTT TAATTATATATTTTCATCCTATAAGCTTAAATAGGAAAGTTTCTTCAACAGGATTAC AGTGTAGCTACCTACATGCTGAAAAATATAGCCTTTAAATCATTTTTATATTATAAC TCTGTATAATAGAGATAAGTCCATTTTTAAAAATGTTTTCCCCAAAC- CATAAAACC CTATACAAGTTGTTCTAG-
TAACAATACATGAGAAAGATGTCTATG-
TAGCTGAAAATA AAATGACGT-
CACAAGAC,
(c) ATGGCAATGGTATCAGAATTCCTCAAG-
CAGGCCTGGTTTATTGAAAAT GAAGAG-
CAGGAATATGTTCAAACTGTGAAGT-
CATCCAAAGGTGGTCCCGGATCAGCG
GTGAGCCCCTATCCTACCTTCAATC-
CATCCTCGGATGTCGCTGCCTT-
GCATAAGGCC ATAATGGTTAAAGGTGT-
GGATGAAGCAACCATCATTGACATT-
CTAACTAAGCGAAAC AATGCACAGCGT-
CAACAGATCAAAGCAGCATATCTCCAG-
GAAACAGGAAAGCCCCTG GAT-
GAAACACTTAAGAAAGCCCTTACAGGT-
CACCTTGAGGAGGTTGTTTTAGCTCTG
CTAAAAACTCCAGCGCAATTTGATGCT-
GATGAACTTCGTGCTGCCAT-
GAAGGGCCTT GGAACTGAT-
GAAGATACTCTAATTGAGATTTTG-
GCATCAAGAACTAACAAAGAAATC
AGAGACATTAACAGGGTCTACAGAGAG-
GAACTGAAGAGAGATCTGG-
CCAAAGACATA ACCTCAGACACATCT-
GGAGATTTTC-
GGAACGCTTTGCTTTCTCTTG-
CTAAGGGTGAC CGATCTGAG-
GACTTTGGTGTGAATGAAGACTTGGCT-
GATTCAGATGCCAGGGCCTTG TAT-
GAAGCAGGAGAAAGGAGAAAGG-
GGACGACGTAAACGTGTTCAATAC-
CATCCTT ACCACCAGAAGCTATC-
CACAACTTCGCAGAGTGTTT-
CAGAAATACACCAAGTACAGT AAG-
GATGACATGAACAAAGTTCTGGACCT-
GGAGTTGAAAGGTGACATT-
GAGAAATGC CTCACAGCTATCGT-
GAAGTGCGCCACAAGCAAAC-
CAGCTTTCTTTGCAGAGAAGCTT CAT-
CAAGCCATGAAAGGTGTTGGAACTCG-
CCATAAGGCATTGATCAGGATTATGGTT
TCCCGTTCTGAAATTGACATGAAT-
GATATCAAAGCATTCTATCAGAAGATG-
TATGGT ATCTCCCTTTGCCAAGC-
CATCCTGGATGAAACCAAAGGAGAT-
TATGAGAAAATCCTG
GTGGCTCTTTGTGGAGGAAAC-
TAAACATTCCCTTGATGGTCTCAAGC-
TATGATCAGA AGACTTTAAT-
TATATATTTTCATCCTATAAGCT-
TAAATAGGAAAGTTTCTTCAACAG GAT-
TACAGTGTAGCTACCTACATGCT-
GAAAAATATAGCCTTTAAATCATTT-
TATAT TATAACTCT-
GTATAATAGAGATAAGTCCATTTTT-
TAAAAATGTTTTCCCCAAACCAT
AAAACCCTATACAAGTTGTTCTAG-
TAACAATACATGAAAGATGTGTCTATG-
TAGCTG AAAATAAAATGACGT-
CACAAGAC,
(d) DNA sequences which hybridize to the foregoing DNA insert or sequences, said hybridizing sequences consisting essentially of DNA sequences which code on expression for a phospholipase inhibitor and
(e) DNA sequences that are degenerate as to the foregoing DNA insert or sequences.

3. The polypeptide according to claim 2, wherein the polypeptide is mature human phospholipase inhibitor protein.

4. The polypeptide according to claim 2, wherein the polypeptide is f-met-human phospholipase inhibitor protein.

5. A substantially pure phospholipase inhibitor consisting essentially of an amino acid sequence selected from the group consisting of: PheLeuPheSerSer-LeuGlnGluGlyArgAspLysAspThrPheSerLysMet Als-MetValSerGluPheLeuLysGlnAlaTrpPheIleGluAsn-GluGluGln GluTyrValGlnThrValLysSerSerLysGly-GlyProGlySerAlavalSer ProTyrProThrPheAsn-ProSerSerAspValAlaAlaLeuHisLysAlaIle MetVal-LysGlyValAspGluAlaThrIleIleAspIleLeuThrLysAr-gAsn AsnAlaGlnArgGlnGlnIleLysAlaAlaTyr-LeuGlnGluThrGlyLysPro LeuAspGluThrLeuLys-LysAlaLeuThrGlyHisLeuGluGluValValLeu
AlaLeuLeuLysThrProAlaGlnPheAspAlaAsp-GlyLeuArgAlaAlaMet LysGlyLeuGlyThrAsp-GluAspThrLeuIleGluIleLeuAlaSerArgThr AsnLys-GluIleArgAspIleAsnArgValTyrArgGlu-
GluLeuLysArgAsp LeuAlaLysAspIleThrSerAspTh-rSerGlyAspPheArgAsnAlaLeuLeu SerLeuAlaLys-GlyAspArgSerGluASpPheGlvvalAsnGluAspLeuAla AspSerAspAlaArgAlaLeuTyrGluAlaGlyGluArgAr-gLysGlyThrAsp ValAsnvalPheAsnThrIleLeuThr-THrArgSerTyrProGlnLeuArgArg ValPheGlnLys-TyrThrLysTyrSerLysHisAspMetAsnLysValLeuAsp LeuGluLeuLysGlyAspIleGluLysCysLeu-
ThrAlaIleValLysCysAla ThrSerLysProAlaPhe-PheAlaGluLysLeuHisGlnAlaMetLysGlyVal Gly-ThrArgHisLysAlaLeuIleArgIleMetvalSerArgSer-GluIleAsp MetAsnAspIleLysAlaPheTyrGlnLysMet-TyrGlyIleSerLeuCysGln AlaIleLeuAspGluThrLys-GlyAspTyrGluLysIleLeuValAlaLeuCys GlyGlyAsn and, MetAlaMetValSerGluPheLeuLysGlnAlaTrp-PheIleGluAsnGluGlu GlnGluTyrValGlnThrValLys-SerSerLysGlyGlyProGlySerAlaVal SerProTyr-ProThrPheAsnProSerSerAspVslAlaAlaLeuHis-LysAla IleMetValLysGlyValAspGluAlaThrIleIleAs-pIleLeuThrLysArg AsnAsnAlaGlnArgGlnGl-nIleLysAlaAlaTyrLeuGlnGlyThrGlyLys ProLeuAsp-GluThrLeuLysLysAlaLeuThrGlyHisLeuGluGluval-Val LeuAlaLeuLeuLysThrProAlaGlnPheAspAlaAsp-GluLeuArgAlaAla MetLysGlyLeuGlyThrAsp-GluAspThrLeuIleGluIleLeuAlaSerArg ThrAsnLys-GluIleArgAspIleAsnArgValTyrArgGlu-
GluLeuLysArg AspLeuAlaLysAspIleThrSerAspTh-rSerGlyAspPheArgAsnAlaLeu LeuSerLeuAlaLys-GlyAspArgSerGlyAsppheGlVValAsnGluAspLeu AlaAspSerAspAlaArgAlaLeuTyrGluAlaGlyGlyAr-gArgLysGlyThr AspValAsnValPheAsn-ThrIleLeuThrThrArgSerTyrProGlnLeuArg ArgVal-PheGlnLysTyrThrLysTyrSerLysHisAspMetAsnLys-ValLeu AspLeuGluLeuLysGlyAspIleGluLysCysLeu-ThrAlaIleValLysCys AlaThrSerLysProAlaPhe-PheAlaGluLysLeuHisGlnAlaMetLysGly ValGly-ThrArgHisLysAlaLeuIleArgIleMetValSerArgSer-GluIle AspMetAsnAspIleLysAlaPheTyrGlnLysMet-TyrGlyIleSerLeuCys GlnAlaIleLeuAspGluThrLys-GlyAspTyrGluLysIleLeuValAlaLeu CysGlyGlyAsn.

6. A pharmaceutically acceptable composition useful in the treatment of arthritic, allergic, dermatologic, ophthalmic, and collagne diseases and other disorders involving inflammatory processes which comprises a pharmaceutically effective amount of at least one polypeptide selected from the group consisting of polypeptides according to claim 1 or 5.

7. A pharmaceutically acceptable composition useful in the treatment of arthritic, allergic, dermatologic, ophthalmic, and collagen diseases and other disorders involving inflammatory processes which comprises pharmaceutically effective amount of at least one polypeptide according to claim 2.

8. A method for treating arthritic, allergic, dermatologic, ophthalmic, and collagen diseases and other disorders involving inflammatory processes which comprises administering a pharmaceutically effective amount of a composition according to claim 6.

9. A method for treating arthritic, allergic, dermatologic, ophthalmic, and collagen diseases and other disorders involving inflammatory processes which comprises administering a pharmaceutically effective amount of a composition according to claim 7.

* * * * *